(12) United States Patent
Daugs

(10) Patent No.: US 7,199,259 B2
(45) Date of Patent: Apr. 3, 2007

(54) RESOLUTION OF α-(PHENOXY)PHENYLACETIC ACID DERIVATIVES

(75) Inventor: Edward D. Daugs, Midland, MI (US)

(73) Assignee: Metabolex, Inc., Hayward, CA (US)

( * ) Notice: Subject to any disclaimer, the term of this patent is extended or adjusted under 35 U.S.C. 154(b) by 226 days.

(21) Appl. No.: 10/656,567

(22) Filed: Sep. 4, 2003

(65) Prior Publication Data
US 2005/0033084 A1    Feb. 10, 2005

Related U.S. Application Data

(60) Provisional application No. 60/608,927, filed on Jun. 20, 2003.

(51) Int. Cl.
*C07C 69/76* (2006.01)

(52) U.S. Cl. .................................................. 560/62

(58) Field of Classification Search .................. None
See application file for complete search history.

(56) References Cited

U.S. PATENT DOCUMENTS

| | | | |
|---|---|---|---|
| 3,378,582 A | 4/1968 | Bolhofer | |
| 3,444,299 A | 5/1969 | Wood et al. | |
| 3,469,009 A | 9/1969 | Klingbail | |
| 3,517,050 A * | 6/1970 | Bolhofer | 260/473 |
| 3,517,051 A * | 6/1970 | Bolhofer | 260/473 |
| 3,558,778 A | 1/1971 | Klingbail | |
| 3,658,829 A | 4/1972 | Nakamura et al. | |
| 3,674,836 A | 7/1972 | Creger | |
| 3,860,628 A | 1/1975 | Shuman | |
| 3,876,791 A | 4/1975 | Hubbard et al. | |
| 3,923,855 A | 12/1975 | Shuman | |
| 3,953,490 A | 4/1976 | Shuman | |
| 4,001,268 A | 1/1977 | Kovar et al. | |
| 4,067,996 A | 1/1978 | Najer et al. | |

(Continued)

FOREIGN PATENT DOCUMENTS

CA    967978    5/1975

(Continued)

OTHER PUBLICATIONS

Jean Jacques and André Collet Enantiomers, Racemates, and Resolutions, pp. 307-328 © 1981 by John Wiley & Sons, Inc.*

(Continued)

*Primary Examiner*—Zachary C. Tucker
(74) *Attorney, Agent, or Firm*—Townsend & Townsend & Crew LLP

(57) ABSTRACT

The present invention provides a method for producing an enantiomerically enriched α-(phenoxy)phenylacetic acid compound of the formula (I):

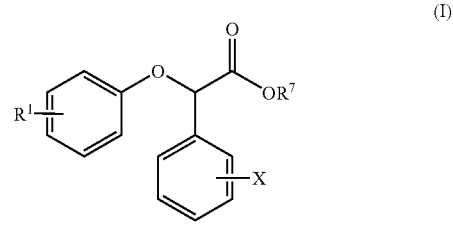

from its enantiomeric mixture, where $R^1$ is alkyl or haloalkyl $R^7$ is heteroalkyl and X is halide.

18 Claims, 20 Drawing Sheets

U.S. PATENT DOCUMENTS

| | | | |
|---|---|---|---|
| 4,146,623 A | | 3/1979 | Parker |
| 4,214,095 A | * | 7/1980 | Thiele et al. .............. 560/57 |
| 4,250,191 A | | 2/1981 | Edwards |
| 4,338,330 A | | 7/1982 | Gillet et al. |
| 4,508,882 A | | 4/1985 | Yoshida et al. |
| 4,528,311 A | | 7/1985 | Beard et al. |
| 4,532,135 A | | 7/1985 | Edwards |
| 4,714,762 A | | 12/1987 | Hoefle et al. |
| 4,786,731 A | * | 11/1988 | Russell .............. 544/354 |
| 4,863,802 A | | 9/1989 | Moore et al. |
| 4,891,396 A | | 1/1990 | Avar et al. |
| 4,910,211 A | | 3/1990 | Imamura et al. |
| 4,933,367 A | | 6/1990 | Wolff et al. |
| 5,132,429 A | | 7/1992 | Narita et al. |
| 5,284,599 A | | 2/1994 | Iwaki et al. |
| 5,476,946 A | | 12/1995 | Linker et al. |
| 5,496,826 A | | 3/1996 | Watson et al. |
| 5,500,332 A | | 3/1996 | Vishwakarma et al. |
| 5,516,914 A | | 5/1996 | Winter et al. |
| 5,554,759 A | | 9/1996 | Vishwakarma |
| 5,700,819 A | | 12/1997 | Aotsuka et al. |
| 5,716,987 A | | 2/1998 | Wille |
| 5,766,834 A | | 6/1998 | Chen et al. |
| 5,859,051 A | | 1/1999 | Adams et al. |
| 5,874,431 A | | 2/1999 | Stevens et al. |
| 5,883,124 A | | 3/1999 | Samid |
| 5,942,626 A | | 8/1999 | Winter et al. |
| 6,013,659 A | | 1/2000 | Goldfarb et al. |
| 6,034,246 A | | 3/2000 | Stevens et al. |
| 6,037,493 A | | 3/2000 | Mathey et al. |
| 6,069,272 A | | 5/2000 | Crout et al. |
| 6,093,830 A | | 7/2000 | Yadav et al. |
| 6,184,235 B1 | | 2/2001 | Connor et al. |
| 6,201,000 B1 | | 3/2001 | Luther et al. |
| 6,201,147 B1 | | 3/2001 | Bornscheuer et al. |
| 6,242,464 B1 | | 6/2001 | Haris et al. |
| 6,248,768 B1 | | 6/2001 | Yamada et al. |
| 6,262,118 B1 | * | 7/2001 | Luskey et al. .............. 514/559 |
| 6,506,747 B1 | | 1/2003 | Betageri et al. |
| 6,613,802 B1 | | 9/2003 | Luskey et al. |
| 6,624,194 B1 | | 9/2003 | Luskey et al. |
| 6,646,004 B1 | | 11/2003 | Luskey et al. |
| 6,670,395 B1 | | 12/2003 | Wille |
| 2003/0220399 A1 | | 11/2003 | Luskey et al. |
| 2004/0039053 A1 | | 2/2004 | Luskey et al. |
| 2004/0204472 A1 | | 10/2004 | Briggs |
| 2005/0033084 A1 | | 2/2005 | Daugs |
| 2005/0075396 A1 | | 4/2005 | Luskey et al. |

FOREIGN PATENT DOCUMENTS

| | | | |
|---|---|---|---|
| EP | 0 077 938 A2 | | 5/1983 |
| EP | 0 105 494 A2 | | 4/1984 |
| EP | 0 306 708 A1 | | 3/1989 |
| EP | 1 162 196 A1 | | 12/2001 |
| FR | 1476525 | | 4/1967 |
| GB | 1182008 | * | 2/1970 |
| GB | 1403309 | | 8/1975 |
| JP | 53-15325 A2 | | 2/1978 |
| JP | 53-71071 A | | 6/1978 |
| JP | 60-109578 A | | 6/1986 |
| WO | WO 92/17435 | | 10/1992 |
| WO | WO 98/23252 A1 | | 6/1998 |
| WO | WO 99/11627 A1 | | 3/1999 |
| WO | WO 00/35886 A3 | | 6/2000 |
| WO | WO 00/74666 A2 | | 12/2000 |
| WO | WO 02/44113 A2 | | 6/2002 |
| WO | WO 04/112774 A1 | | 12/2004 |

OTHER PUBLICATIONS

Read and Reid, "The Complete Optical Resolution of Externally Compensated Acids and Bases" Journal of the Society of the Chemical Industry—London, vol. 47, pp. 8T-11T (1928).*

Aronow, W.S. et al., "Effect of halofenate on serum uric acid," Clin. Pharmacol. Ther., 1973, vol. 14, pp. 371-373.

Aronow, W.S., et al., "Halofenate: An Effective Hypolipemia- and Hypouricemia-Inducing Drug", Current Therapeutic Research, 1973, vol. 15, No. 12, pp. 902-906.

Bardin, C.W., eds., Current Therapy in Endocrinology and Metabolism, 6th Edition, Mosby - Year Book, Inc., St. Louis, MO, 1997, pp. 509-519.

Barrett-Conner, "Epidemology, Obesity, and Non-Insulin-Dependent Diabetes Mellitus", Epidemol. Rev., 1989, vol. 11, pp. 172-181.

Bassett, D.R., et al., "Effects of halofenate and probenecid in serum lipids and uric acid in hyperlipidemic, hyperuricemic adults," Clin. Pharmacol. Ther. 1977, vol. 22, No. 3, pp. 340-351.

Bell, G., et al., "Glucokinase Mutations, Insulin secretion, and Diabetes Mellitus," Annu. Rev. Physiol., 1996, vol. 58, No. pp. 171-187.

Berkow, R., Chapter 94, "Disorders of Carbohydrate Metabolism," The Merck Manual of Diagnosis and Therapy 15th ed., *Merck Sharp & Dohme Research Laboratories*, 1987, pp. 1069-1072.

Bluestone, R., et al., "Halofenate *Its Selection and Trial as a Primary Uricosuric Agen"t*, Arthritis Rheum., 1975, vol. 18, pp. 859-862.

Brooks, D., et al., "Design and Synthesis of 2-Methyl-2-4{(4-(2-(5-methyl-2-aryloxazol-4-yl)ethoxy}phenoxy'-propionic Acids: A New Class of Dual PPARα/y Agonists, " J. Med. Chem., 2001, vol. 44, pp. 2061-2084.

Chiasson, J., et al., "The Efficacy of Acarbose in the Treatment of Patients with Non-Insulin-dependant Diabetes Mellitus," Annals of Intern. Med., 1994 vol. 121, No. 12, pp. 928-935.

Coniff, R., et al., "Acarbose: A Review of US Clinical Experience," Clinical Therapeutics, 1997, vol. 19, No. 1, pp. 16-26.

Coniff, R., et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus," The American Journal of Medicine, 1995, vol. 98, pp. 443-451.

Diamant, M., et al., "Thiazolidinediones in type 2 diabetes mellitus: current clinical evidence," Drugs, 2003, vol. 63, pp. 1373-1405. ABSTRACT.

Dorfler, H., "Primarer Verteilungraum and Plasmahalbwertszeit von intravenos verbreichtem Insulin," Med. Poliklinik Univ. Muchen, 1973, pp. 1297-1299.

Edelman, S.V., et al., "Non-Insulin-Dependent Diabetes Mellitus", Current Therapy in Endocrinology and Metabolism, 1997, pp. 430-438.

El-Sherief, et al., "Synthesis and Antimicrobial Activities of Some New Benzimidazoles, Part 1," Bull. Fac. Sci. Assiut Univ. B, 1995, vol. 24, No. 1, pp. 111-123.

Fajans, S., et al., "Maturity Onset Diabetes of the Young (MODY)" Diabetes Medicine, 1996, vol. 13, pp. S90-S95.

Fanelli, G.M., Jr., "Renal Excretion and Uricosuric Properties of Halofenate A Hypolipidemic Uricosuric Agent in the Chimpanzee," J. Pharmacol. Exp. Ther. 1972, vol. 180, pp. 377-396.

Feldman, E.B., et al., "Effects of Halofenate on Glucose Tolerance in Patients with Hyperlipoproteinemia," Journal Clinical Pharmacology, 1978, vol. 18, pp. 241-248.

Feldman, E.B., et al., "Insulin Sensitivity in Hypertriglyceridemia: induction by combined triglyceride and uric lowering," Clinical Research, 1975, vol. 23, No. 1, pp. 43A.

Flier, J., "Insulin Receptors and Insulin Resistance," Ann Rev. Med., 1983, vol. 34, pp. 145-161.

Friedberg, S.J., "The Control of Insulin Resistant and Refractory Type II Diabetes Mellitus by Means of Halofenate-Sulfonylurea Combined Regimen," Clinical Research, 1986, vol. 34, pp. 682A.

Gavin III, J.R., et al., "Report of the Expert Committee on the Diagnosis and Classification of Diabetes Mellitus," Diabetes Care, 1999, vol. 22, Supplement 1, pp. S5-S19.

Goetze, S., et al., "PPARy-Ligands Inhibit Migration Mediated by Multiple Chemoattractants in Vascular Smooth Muscle Cells," Journal of Cardiovascular Pharmacology, 1999, vol. 33, pp. 798-806.

Howard, B., et al., "Lipoprotein Composition in Diabetes Mellitus," Atherosclerosis, 1978, vol. 30, pp. 153-162.

Huang, et al., "Search for New Antiphytovirucides," J. Wuhan Univ. (Nature Science Edition), 1995, vol. 41, No. 2, pp. 142-148.

Hucker, H.B., et al., "Metabolism of a New Hypolipidemic Agent, 2-Acetamidoethyl (p-Chlorophenyl) (m-Trifluoromethylphenoxy)-Acetate (Halofenate) in the Rat, Dog, Rhesus Monkey and Man," The Journal of Pharmacology and Experimental Therapeutics, 1971, vol. 179, No. 2, pp. 359-371.

Hutchison, J.C., et al., "The Uricosuric Action of Halofenate (MK-185) in Patients with Hyperuricemia or Uncomplicated Primary Gout and Hyperlipidemia," Atheroscierosis, 1973, vol. 18, pp. 353-362.

Iwamoto, Y., et al., "Effect of Combination Therapy of Troglitazone and Sulphonylureas in Patients with Type 2 Diabetes Who Were Poorly Controlled by Sulphonylurea Therapy Alone," Diabetic Medicine, 1996, vol. 13, pp. 365-370.

Jacques, J., et al., "Formation and separation of diasteromers." in Enantiomers, Racemates, and Resolutions, pp. 251-328, John Wiley and Sons, New York (1981).

Jain, A., et al., "Potentiation of Hypoglycemic Effect of Sulfonylureas by Halofenate," New England J. of Med., 1975, vol. 293, No. 25, pp. 1283-1286.

Jain, A., et al., "The effect of MK-185 on some aspects of uric acid metabolism," Clin. Pharmacol. Ther., 1970, vol. 11, pp. 551-557.

Joslin, E., "Arteriosclerosis and Diabetes," Annals of Clinical Medicine, 1927, vol. 5, No. 12, pp. 1061-1079.

Keller C. et al., "Die Behnandlung von Hyperlipidämie und Hyperurikämie mit 2-Acetamidoäthyl-(4-chlorophenyl)-(3-trifluoromethylphenoxy)-acatat (Halofenat), einem Derivat des Clofibrat," Arzneimittelforschung, 1976, vol. 26, No. 12 pp. 2221-2224.

Knowler, et al., "Obesity in the Pima Indians: its magnitude and relationship with diabetes," Am. J. Clin. Nutr., 1991, vol. 53, pp. 1543-1551.

Kobayashi, M., et al., "Improvement of Glucose Tolerance in NIDDM by Clofibrate Randomized Double-Blind Study," Diabetes Care, vol. 11, No. 6, 1988, pp. 495-499.

Kohl, E. A., et al., "Improved Control of Non-insulin-dependent Diabetes Mellitus by Combined Halofenate and Chlorpropamide Therapy," Diabetes Care, 1984, vol. 7, No. 1, pp. 19-24.

Kreisberg, R.A., "Hyperlipidemia," Current Therapy in Endocrinology and Metabolism 6th Edition, 1997, pp. 509-519.

Krut, L. H., et al., "Comparision of Clofibrate with Halofenate in Diabetics with Hyperlipidaemia," S.A. Med. J., 1977, pp. 349-352.

Kudzma, D.J., et al., "Potentiation of Hypoglycemic Effect of Chlorpropamide and Phenformin by Halofenate," Diabetes, 1977, vol. 26, No. 4, pp. 291-295.

Kuntznen Von O. et al., "Wirkung von Halofenat auf Triglycerid- und Harnsäurespiegel sowie auf Gerinnungsund Thrombozytenverhalten bei Patienten mit Hyperlipoproteinämie Typ IV und Hyperurikämie," Arzneimittelforschung, 1978, vol. 28, No. 12, pp. 2349-2352.

Kwiterovich, P., "State-of-the-Art Update and Review: Clinical Trials of Lipid-Lowering Agents," The American Journal of Cardiology, 1998, vol. 82, No. 12A, pp. 3U-17U.

Leroith, D. et al. (eds.), Diabetes Mellitus, Lippincott-Raven Publishers, Philadelphia, PA U.S.A. (1996).

Lin, J.H., et al., "Inhibition and Induction of Cytochrome P450 and the Clinical Implications," Clin Pharmacokinet, 1998, vol. 35, pp. 361-390.

Lisch, H.J., et al., "Comparison of the Effects of Halofenate (MK-185) and Clofibrate on Plasma Lipid and Uric Acid Concentration in Hyperlipoprpteinemic Patients," Atherosclerosis, 1995, vol. 21, pp. 391-399.

Lochmüller, et al., "Chromatographic resolution of enantiomers." J. Chromatography 113:283-302 (1975).

Mahley, R. W., et al., Disorders of Lipid Metabolism, Williams Textbook of Endocrinology, 1998, pp. 1099-1153.

Malher, R., Clinical Review 102, "Type 2 Diabetes Mellitus: Update on Diagnosis, Pathophysiology, and Treatment," J. Clin. Endocrinol. Metab., 1999, vol. 84, No. 4, pp. 1165-1171.

Mandel, Lewis, "Studies on the Mechanism of Action of Halofenate," Lipids, 1976, vol. 12, No. 1., pp. 34-43.

McMahon, et al., "Some Effects of MK-185 on Lipid and Uric Acid Metabolism in Man," Univ. Mich. Med. Center J., 1970, vol. 36, No. 4, pp. 247-248.

Metabolex, The Diabetes Biopharmaceutical Company, "Metabolic Diseases Drug Discovery & Development Summit," Strategic Research Institute, (May 6-7, 2002).

Miners, J.O., et al., "Cytochrome P4502C9: an enzyme of major importance in human drug metabolism," J Clin Pharmacol, 1998, vol. 45, pp. 525-538.

Morgan, J. P., et al., "Hypolipidemic, uricosuric, and thyroxine-displacing effects of MK-185 (halofenate)," Clin. Pharmacol. Therap., 1971, vol. 12, No. 3, pp. 517-524.

Neuman, J., et al., "A double-blind comparison of the hypolipidemic and hypouricemic action of halofenate and clofibrate in patients with hyperlipoprteinemia," The International Cardiovascular Society, pp. 532-537.

Pelkonen, O., et al., "Inhibition and induction of human cytochrome P450 (CYP) enzymes," Xenobiotica, 1998. vol. 28, No. 12, pp. 1203-1253.

Qu, et al., "Search for New Anitphytovirucides," Wujan Univ. Journal of National Science, 1998, vol. 3, No. 2, pp. 201-204.

Qu, et al., "Some New Antiphytoviral Compounds Containing Trifluoromethyl Group," Wuhan Univ. Journal of National Science, 1996, vol. 1, No. 2, pp. 283-284.

Ravenscroft, P.J., et al., "Studies of the uricosuric action of the hypolipidemic drug halofenate," Clin. Pharmacol. Ther., 1973, vol. 14, No. 4, pp. 547-551.

Reaven, G. M., "Insulin Resistance and Human Disease: A Short History," J. Basic & Clin. Phys. & Pharm., 1998, vol. 9, No. 2-4, pp. 387-406.

Reaven, G. M., "Pathophysiology of Insulin Resistance in Human Disease," Physiol. Rev. 1995, vol. 75, No. 3, pp. 473-486.

Ryan, J. R., "The metabolic spectrum of halofenate," Int. J. Clin. Pharmacol., 1975, vol. 12, No. 1/2, pp. 239-243.

Safak, et al., "Synthesis of Some Benzimidazol Derivatives, and Their Effects on Serum Total Cholesterol and Trigliceride Levels in Rats," FABAD J. Farm. Sci., 1983, vol. 8, No. 1, pp. 19-29.

Schaeffer, S. "Trying to beat PPAR," BioCentury, The Bernstein Report on BioBusiness, (Reprint from Jun. 14, 2004) pp. 1-3.

Schapel, G.J., et al., "Efficacy and Interactions of Oxandrolone, Halofenate and Clofibrate in a Factorial Study on Experimental Acute Nephrotic Hyperlipidemia," The Journal of Pharmacology and Experimental Therapeutics, 1975, vol. 194, No. 1, pp. 274-284.

Schlosstein, L.H., et al. "Studies with some novel uricosuric agents and their metabolites: correlation between clinical activity and drug-induced displacement of urate from its albumin-binding sites," J. Lab. Clin. Med., vol. 82, No. 3, pp. 412-418.

Sirtori, C., et al., "Clinical Evaluation of MK-185: A New Hypolipidemic Drug," Lipids, 1971, 7, No. 2, pp. 96-99.

Skyler, J.S., "Glucose Control in Type 2 Diabetes Mellitus," Annals of Internal Medicine, 1997, vol. 127, No. 9, pp. 837-838.

Steiner, A., et al., "A Comparative Review of the Adverse Effects of Treatments for Hyperlipidaemia," Drug Safety, 1991, vol. 6, No. 2, pp. 118-130.

Taskinen, M.R., "Lipid disorders in NIDDM: implications for treatment," Journal of Internal Medicine, 1998, vol. 244, pp. 361-370.

Trust, R. I., et al., "(Aryloxy)[p-(aryloxy)phenyl]- and (Aryloxy)[p-arylthio)phenyl]acetic Acids and Esters as Hypolipidemic Agents," Journal of Medicinal Chemistry, 1979, vol. 22, No. 9, pp. 1068-1074.

Turner, N., et al., "Insulin resistance, impaired glucose tolerance and non-insulin-dependent diabetes, pathologic mechanisms and treatment: Current status and therapeutic possibilities," Prog Drug Res., 1998, pp. 33-94.

Varma, et al., "Synthesis of Substituted 2-Phenylbenzothiazoles & 5(6)-Nitro- 1, 3-disubsituted-benzimidazoline-2-thiones as CNS Active Agents," Indian Journal of Chemistry, 1988, vol. 27B, No. 5, pp. 438-442.

Vedell, E.S., et al., "Differential Effects of Chronic Halofenate Administration on Drug Metabolism in Man," Fed. Proc., 1972, vol. 31, No. 2, p. 538.

Wilson, J., et al., (ed.) Disorders of Lipid Metabolism, Chapter 23, Textbook of Endocrinology, 9th Edition, 1998, W.B. Sanders Company, Philadelphia, PA. (all references cited therein).

Wolfram, G. et al., "Primarer Verteilungrsaum und Plasmahalhwertszeit von intravenos verabreichtem Insulin," Verh. Dtsch. Ges. Inn. Med., 1973, vol. 79, No. 1, pp. 291-1293.

Wright, A.D., et al., "UKPDS 28: A Randomized Trail of Efficacy of Early Addition of Metformin in Sulfonylurea-Treated Type 2 Diabetes," Diabetes Care, 1998, vol. 21, pp. 87-92.

* cited by examiner

| Exp. # | Charge g iPA/ gCPTA | Charge mole base/ mole CPTA | Nucl'n Temp. | Isolation Temp & Hold Time | Product Isolation: Ratio of % (-)-CPTA Crystal | Product Isolation: Ratio of % (-)-CPTA M.L. | Calculated % Yield of (-)-CPTA | Comments |
|---|---|---|---|---|---|---|---|---|
| 1 | 4.11 | 0.57 | 61° | 17° + 6hr | 79.9 | 27.0 | 69.5 | (+)-Salt nucleation at 22° |
| 2 | 4.11 | 0.55 | 59° | 22° + 8hr | 77.9 | 28.3 | 68.2 | (+)-Salt nucleation after 1 hr at 22° |
| 3 | 4.11 | 0.90 | 59° | 40° | 99.2 | 27.7 | 61.9 | initially added 0.15 eq. triethylamine |
| 4 | 5.50 | 0.75 | 61° | 22° + 10hr | 66.4 | 30.7 | 71.8 | (+)-Salt nucleation at 40° |
|  |  |  |  | to 28° | 68.2 | 28.8 | 73.4 |  |
|  |  |  |  | to 35° | 71.4 | 29.1 | 70.6 |  |
|  |  |  |  | to 43° | 77.0 | 29.9 | 65.7 |  |
|  |  |  |  | to 51° | 95.0 | 30.3 | 57.9 |  |
|  |  |  |  | to 55° | 99.4 | 33.0 | 50.9 |  |
| 5 | 4.11 | 0.52 | 61° | 13° + 8hr | 99.7 | 20.9 | 73.6 | (+)-Salt nucleation 3 hr after sample |
|  |  |  |  | +30hr(13°) | 83.3 | 24.9 | 71.6 |  |
| 6 | 3.14 | 0.52 | 59° | 1° | 98.7 | 23.5 | 69.6 |  |
|  |  |  |  | +20hr(1°) | 98.2 | 19.4 | 76.3 |  |
|  |  |  |  | to 17° + 9hr | 81.2 | 25.3 | 71.8 |  |
| 7 | 5.50 | 0.90 | 64° | 3° + 1hr | 66.4 | 25.5 | 79.6 | initially added 0.04 eq. KOH |
|  |  |  |  | to 22° + 10hr | ~56 | 25.5 | 90.0 |  |
| 8 | 3.53 | 0.55 | 59° | 22° + 5hr | 78.6 | 26.0 | 71.7 | (+)-Salt nucleation at 30° |
| 9 | 3.93 | 0.45 | 59° | 22° + 4hr | 99.6 | 24.3 | 68.0 |  |
|  |  |  |  | + 12hr(22°) | 99.5 | 22.9 | 70.4 |  |
|  |  | 0.52 (added base) |  | (22°) + 3hr | 89.4 | 24.6 | 70.1 | (+)-Salt nucleating, not at equilibrium |
|  |  | 0.49 (added CPTA) |  | (22°) + 22hr | 84.3 | 25.9 | 69.6 |  |
| 10 | 3.53 | 0.52 | 59° | 22° + 10hr | 73.9 | 25.5 | 74.8 | (+)-Salt nucleation at 25° |
| 11 | 3.93 | 0.45 | 54° | 22° + 14hr | 99.1 | 22.6 | 71.0 |  |
|  |  | 0.48 (added base) |  | 22° + 24hr | 89.2 | 24.7 | 70.0 |  |
| 12 | 3.93 | 0.43 | 52° | 21° | 99.5 | 27.5 | 62.2 |  |
|  |  |  |  | + 16hr(21°) | 99.4 | 23.9 | 68.7 | seeded with (+)-Salt after sample |
|  |  |  |  | +8hr(22°) | 99.3 | 23.7 | 69.1 |  |
|  |  | 0.45 (added base) |  | 22° + 14hr | 98.9 | 22.5 | 71.2 | seeded with (+)-Salt after samlple |
|  |  |  |  | +6hr(22°) | 98.7 | 22.3 | 71.61 |  |
|  |  | 0.47 (added base) |  | 22° + 14hr | 96.8 | 21.9 | 72.6 | seeded with (+)-Salt after sample |
|  |  |  |  | +23hr(22°) | 92.3 | 23.4 | 71.3 |  |
| 13 | 3.14 | 0.38 | 59° | 17° + 8hr | 99.4 | 27.2 | 62.8 |  |
|  |  |  |  | to -10° + 19hr | 99.8 | 24.3 | 67.9 | seeded with (+)-Salt after reaching 10° |

FIG. 2

| Temperature | Measured Component | Experimental Result | Calculation By Model |
|---|---|---|---|
| 21.5 °C | Ratio % (-) - CPTA in crystal | 66.4% | 63.9% |
| | Ratio % (-) - CPTA in mother liquor | 30.7% | 28.5% |
| | % (-) - CPTA yield | 71.8% | 72.8% |
| 28.3 °C | Ratio % (-) - CPTA in crystal | 68.2% | 68.2% |
| | Ratio % (-) - CPTA in mother liquor | 28.8% | 28.7% |
| | % (-) - CPTA yield | 73.4% | 73.6% |
| 35.1 °C | Ratio % (-) - CPTA in crystal | 71.4% | 71.4% |
| | Ratio % (-) - CPTA in mother liquor | 29.1% | 28.9% |
| | % (-) - CPTA yield | 70.6% | 70.8% |
| 42.5 °C | Ratio % (-) - CPTA in crystal | 77.0% | 76.7% |
| | Ratio % (-) - CPTA in mother liquor | 29.9% | 29.1% |
| | % (-) - CPTA yield | 65.7% | 67.4% |
| 51.1 °C | Ratio % (-) - CPTA in crystal | 95.0% | 87.3% |
| | Ratio % (-) - CPTA in mother liquor | 30.3% | 29.2% |
| | % (-) - CPTA yield | 57.9% | 62.4% |
| 55.3 °C | Ratio % (-) - CPTA in crystal | 99.4% | 96.1% |
| | Ratio % (-) - CPTA in mother liquor | 33.0% | 29.3% |
| | % (-) - CPTA yield | 50.9% | 59.6% |

FIG. 6

(-)-CPTA • CAF D Base Salt ,m.p. 180.5 - 181.5

| | | | | | Calculated Values | | | | |
|---|---|---|---|---|---|---|---|---|---|
| Solvent | Temp. °C | grams tare | grams w/soln | grams evap'd | grams soln volat. solv | grams solvent | grams solids | grams CPTA | grams solute | Wt% solute | wt%solute in evapSolv | g solute/ g evap solv |
| iPA w/CPTA | 36 | 17.2900 | 18.0100 | 17.3895 | 0.7200 | 0.6205 | 0.0995 | 0.0767 | 0.0228 | 3.17% | 3.55% | 0.036755 |
| iPA w/CPTA | 24 | 16.7808 | 17.5728 | 16.8840 | 0.7920 | 0.6888 | 0.1032 | 0.0851 | 0.0181 | 2.28% | 2.56% | 0.026226 |
| iPA w/CPTA | 10 | 17.2556 | 18.1769 | 17.3702 | 0.9213 | 0.8067 | 0.1146 | 0.0997 | 0.0149 | 1.62% | 1.81% | 0.01846 |
| iPA w/CPTA | -1 | 17.1063 | 17.9898 | 17.2131 | 0.8835 | 0.7767 | 0.1068 | 0.0960 | 0.0108 | 1.22% | 1.37% | 0.013905 |
| | | | | | | | | | | | | |
| EtOH w/CPTA | 36 | 17.1900 | 17.9419 | 17.3577 | 0.7519 | 0.5842 | 0.1677 | 0.0912 | 0.0765 | 10.18% | 11.58% | 0.130959 |
| EtOH w/CPTA | 24 | 17.2524 | 17.9330 | 17.3813 | 0.6806 | 0.5517 | 0.1289 | 0.0861 | 0.0428 | 6.29% | 7.20% | 0.077541 |
| EtOH w/CPTA | 10 | 17.2977 | 18.1608 | 17.4587 | 0.8631 | 0.7021 | 0.1610 | 0.1096 | 0.0514 | 5.96% | 6.82% | 0.073212 |
| EtOH w/CPTA | -1 | 17.1536 | 18.2098 | 17.3383 | 1.0562 | 0.8715 | 0.1847 | 0.1360 | 0.0487 | 4.61% | 5.29% | 0.066833 |

(+)-CPTA • CAF D Base Salt

| | | | | | Calculated Values | | | | |
|---|---|---|---|---|---|---|---|---|---|
| Solvent | Temp. °C | grams tare | grams w/soln | grams evap'd | grams soln | grams solvent | grams solids | grams CPTA | grams solute | Wt% solute | wt%solute in evapSolv | g solute/ g evap solv |
| iPA w/CPTA | -2 | 17.2325 | 17.8545 | 17.3147 | 0.6220 | 0.5398 | 0.0822 | 0.0667 | 0.0155 | 2.49% | 2.79% | 0.028679 |
| iPA w/CPTA | 10 | 17.1810 | 17.7942 | 17.2649 | 0.6132 | 0.5293 | 0.0839 | 0.0654 | 0.0185 | 3.01% | 3.37% | 0.034911 |
| iPA w/CPTA | 22 | 17.2838 | 18.0462 | 17.4053 | 0.7624 | 0.6409 | 0.1215 | 0.0792 | 0.0423 | 5.55% | 6.19% | 0.065977 |
| iPA w/CPTA | 36 | 17.1474 | 17.8976 | 17.2742 | 0.7502 | 0.6234 | 0.1268 | 0.0771 | 0.0497 | 6.63% | 7.39% | 0.079801 |
| iPA w/CPTA | 10 | 17.2816 | 17.4692 | 17.3074 | 0.1876 | 0.1618 | 0.0258 | 0.0200 | 0.0058 | 3.09% | 3.46% | 0.035856 |
| | | | | | | | | | | | | |
| EtOH w/CPTA | -2 | 17.3289 | 18.5380 | 17.6105 | 1.2091 | 0.9275 | 0.2816 | 0.1448 | 0.1368 | 11.32% | 12.85% | 0.147512 |
| EtOH w/CPTA | 10 | 17.2118 | 17.9940 | 17.4089 | 0.7822 | 0.5851 | 0.1971 | 0.0913 | 0.1058 | 13.52% | 15.31% | 0.180765 |
| EtOH w/CPTA | 22 | 17.2095 | 18.0054 | 17.4362 | 0.7959 | 0.5692 | 0.2267 | 0.0889 | 0.1378 | 17.32% | 19.50% | 0.242178 |
| EtOH w/CPTA | 36 | 17.2133 | 17.9657 | 17.4487 | 0.7524 | 0.5170 | 0.2354 | 0.0807 | 0.1547 | 20.56% | 23.03% | 0.299219 |

FIG. 10A

| Eq. Base | Predicted k | Regression k used | Regression % (+)-Salt | Free CPTA, Ratio % (+) |
|---|---|---|---|---|
| 0.75 | <1 | 0.68 | 41.9 | 25.8 |
| 0.57 | <1 | 0.85 | 31.4 | 25.3 |
| 0.52 | <1 | 0.70 | 25.7 | 23.7 |
| 0.52 | >1 | 0.60 | 26.1 | 24.1 |
| 0.48 | >1 | 0.50 | 21.5 | 23.7 |

Experimental Data for Figure 6

FIG. 10A (CONT.)

| Eq Base | | (+) | | k Factor | | | | Salt in IPA+CPTA | | | | | | |
|---|---|---|---|---|---|---|---|---|---|---|---|---|---|---|
| 0.75 | | 0.3146 | 41.9% | | orig | | | ln(S) = a + bT | | e^a = | 0.019509 | 0.009663 | 0.01421 | orig |
| | | 0.4354 | 58.1% | | new | | | S = e^a · e^bT | | a = | -3.93687 | -4.63947 | 0.009663 | new |
| Basis: Salt in Solvent | | | | | | | | | | b = | 0.02771 | 0.02613 | | |
| | | Wt Fract | Feed | Feed | | G(+)/ | G(-)/ | Calc soluble | Calc insoluble | Calc °C Temp of | Calc soluble | Calc insoluble | ML ratio | actual insoluble |
| g IPA /g Solute | | solute | %(+) | %(-) | | GIPA | GIPA | (+) | (-) | (+) Sat'n | (-) | (+) | (+) | (+) |
| 4.465696 | | 0.182959 | 0.419467 | 0.580533 | | 0.093931 | 0.129998 | 0.042738 | 0.051193 | 56.72 | 0.020242 | 0.109756 | 67.86% | 0.05119 |
| | | | | | | | | (based on Avail. (-)) | | | | | | |
| | | | | | | | | Crystal Yield | %(+) in Xtal | Calc °C Temp of (-) Sat'n | %(-) in Xtal | salt grav yield | | |
| | | | | | | | | 123.8% | 31.81% | 68.19% | | 99.47 | 71.9% | |
| | | | | Mass Balance for 100g CPTA Fed | | Salt | | CPTA | grams | Ratio% | | | | |
| | | | | | salt | saltML | sum | in ML | overallML | overallML | | | | |
| | | | | (-)ratio | 68.19299 | 32.14063 | | | | | | | | |
| | | | | (+)ratio | 31.80701 | 67.85937 | | | | | | | | |
| | | | | weight | 0.539064 | 0.210936 | | | | | | grav yield from CPTA = | 53.9% | |
| | | | | | | | | | | Ratio % | | (-)yield from CPTA = | 36.8% | |
| | | | | 100g total CPTA feed | | | | | | | | | | |
| | | | | g (-) | 36.76038 | 6.779616 | 43.54 | 6.46 | 25.8% | 28.7% | | | | |
| | | | | g (+) | 17.14601 | 14.31399 | 31.46 | 18.54 | 74.2% | 71.3% | | | | |
| | | | | total | 53.9064 | 21.0936 | 75 | 25 | | | 46.0936 | | | |

FIG. 10B

| Exp. # | MolRatio Base | g IPA/ g CPTA | Cool at °C/min | Final T°C | Solid % (−) | Solid % (+) | M.L. % (−) | M.L. % (+) | %Yield Calc | %Yield Overall | %Yield Actual |
|---|---|---|---|---|---|---|---|---|---|---|---|
| 1 | 0.53 | 4.00 | 0.25 | 4 | 90.72 | 9.28 | 20.61 | 79.39 | 41.9 | | |
| Recrystallization | | 4.00 | 0.25-1.0 | 2 | 99.38 | 0.62 | 42.60 | 57.40 | 84.7 | 35.5 | 34.5 |
| 2 | 0.50 | 6.17 | 0.05 | −3 | 98.05 | 1.95 | 24.05 | 75.95 | 35.1 | 35.1 | 33.6 |
| 3 | 0.53 | 4.00 | 0.25 | 0 | 73.14 | 26.86 | 28.88 | 71.12 | 47.7 | | |
| Recrystallization | | 4.00 | 1.0 | 11 | 98.20 | 1.80 | 22.62 | 77.38 | 66.8 | 31.9 | 33.0 |
| 4 | 0.54 | 4.00 | 0.25 | −4 | 79.72 | 20.28 | 26.62 | 73.38 | 44.0 | | |
| Recrystallization | | 3.63 | 0.08 | 4 | 99.07 | 0.93 | 23.22 | 76.78 | 74.5 | 32.8 | 32.8 |
| 5 | 0.53 | 4.00 | 0.5 | −11 | 93.70 | 6.30 | 26.00 | 74.00 | 35.4 | | |
| Recrystallization | | 3.93 | 0.5 | −3 | 99.68 | 0.33 | 46.42 | 53.58 | 88.8 | 31.5 | 31.6 |
| 6 | 0.53 | 3.98 | 0.25 | −3 | 90.88 | 9.12 | 26.95 | 73.05 | 36.1 | | |
| Recrystallization | | 4.98 | 0.1 | 4 | 99.42 | 0.58 | 23.85 | 76.15 | 88.7 | 32.0 | 31.5 |
| 7 | 0.54 | 4.08 | 0.3 | −3 | 96.00 | 4.00 | nd | nd | | | |
| Recrystallization | | 4.24 | 0.4 | 4 | 99.86 | 0.14 | 57.41 | 42.59 | 90.9 | | 31.2 |
| 8 | 0.53 | 4.00 | 0.25 | −8 | 73.54 | 26.46 | 28.09 | 71.91 | 48.2 | | |
| Recrystallization | | 3.96 | 0.3 | 11 | 98.57 | 1.43 | 21.84 | 78.16 | 67.4 | 32.5 | 31.1 |
| 9 | 0.50 | 3.88 | 0.08 | −7 | 76.83 | 23.17 | 28.96 | 71.04 | 43.9 | | |
| Recrystallization | | 4.62 | 0.5 | 5 | 98.48 | 1.52 | 24.91 | 75.09 | 70.6 | 31.0 | 30.7 |
| 10 | 0.50 | 3.90 | 0.05 | 0 | 96.15 | 3.85 | 26.07 | 73.93 | 34.1 | | |
| Recrystallization | | 4.80 | 0.3 | 3 | 99.86 | 0.14 | 70.32 | 29.68 | 87.4 | 29.9 | 30.6 |
| 11 | 0.55 | 6.16 | 0.2 | 5 | 73.92 | 26.08 | 41.08 | 58.92 | 56.4 | | |
| Recrystallization | | 4.38 | 0.08 | 12 | 99.31 | 0.69 | | | | | 29.1 |
| 12 | 0.56 | 4.99 | 0.1 | 2 | 78.92 | 21.08 | 28.04 | 71.96 | 43.2 | | |
| Recrystallization | | 5.00 | 0.25 | 4 | 84.47 | 15.53 | 29.29 | 70.71 | 89.9 | (38.8) | (38.3) |
| Recrystallization | | 5.00 | 0.25 | 12 | 99.44 | 0.56 | 30.30 | 69.70 | 78.4 | 30.4 | 28.2 | nd - Not Determined

| Exp. # (Fig. 1) | Initial T °C | Rate °C/min | Final T °C | Hrs at < 10 °C | Holding Period Profile | Solid % (-) | Solid % (+) | M.L. % (-) | M.L. % (+) | % Yield (-)-CPTA |
|---|---|---|---|---|---|---|---|---|---|---|
| 1 | 60 | 0.25 | 4 | 14 | 13h at 4C | 90.72 | 9.28 | 20.61 | 79.39 | 38.0 |
| 8 | 60 | 0.25 | -5 | 20 | 11h to 10C, 3h to -8C, 5h at -8C | 73.54 | 26.46 | 28.09 | 71.91 | 35.5 |
| 4 | 55 | 0.25 | -4 | 3 | 1h at -4C | 79.72 | 20.28 | 26.62 | 73.38 | 35.1 |
| 3 | 60 | 0.25 | -2 | 16 | 11h to 10C; 1h to -2C; 4h at -2C | 73.14 | 26.86 | 28.88 | 71.12 | 34.9 |
| 2 | 55 | 0.05 | -3 | 5 | 1h at -3C | 98.05 | 1.95 | 24.05 | 75.95 | 34.4 |
| 12 | 55 | 0.10 | 1 | 13 | 9h to 10C, 1h to 1C; 4h at 1C | 78.92 | 21.08 | 28.04 | 71.97 | 34.1 |
| 9 | 65 | 0.075 | 0 | 8 | 3h at 0C; 1h to -7C; 2h at -7C | 76.83 | 23.17 | 28.96 | 71.04 | 33.8 |
| 5 | 60 | 0.5 | -11 | 2.5 | 1.5h at -11C | 93.70 | 6.30 | 26.00 | 74.00 | 33.2 |
| 10 | 55 | 0.05 | 0 | 4 | 1h at 0C | 96.15 | 3.85 | 26.07 | 73.93 | 32.8 |
| 5 | 55 | 0.25 | -3 | 2 | 1h at -3C | 90.88 | 9.12 | 26.95 | 73.05 | 32.8 |

FIG. 15

| | %ee CPTA | %ee (-)-halofenate | HPLC Area% Crude CPTA | HPLC Area% Crude Halofenate | HPLC Area% Isolated CPTA | HPLC Area% Isolated Halofenate | Yield | mol % in ML CPTA | mol % in ML Halofenate |
|---|---|---|---|---|---|---|---|---|---|
| 1 | 97.1 | 99.9 | 6.1 | 85.2 | 0.72 | 98.93 | 55% | 5.8% | 38% |
| 2 | 99.3 | >99.8 | 5.5 | 89.6 | 0.60 | 99.40 | 52% | 5.9% | 41% |
| Second Crop | | 99.6 | 6.1 | 45.0 | 3.89 | 89.93 | 21% | 4.3% | 13% |
| 3 | 99.2 | 99.7 | 7.1 | 85.3 | 0.40 | 99.29 | 55% | 7.5% | 34% |
| 4 | 98.6 | 99.8 | 3.9 | 91.8 | 0.10 | 99.90 | 47% | 3.1% | 40% |
| Second Crop | | 98.8 | 6.1 | 82.5 | 3.22 | 89.65 | 33% | nd | nd |
| 5 | 99.7 | 99.7 | 8.0 | 83.2 | 0.64 | 99.18 | 59% | nd | nd | nd - Not Determined

FIG. 18

| Recovered From: | Wt% Aqueous Sln | pH | mp °C | Recovery | (+)/(-) Ratio |
|---|---|---|---|---|---|
| Diastereomeric Salt | 20.4 | 12.4 | 157.2-158.0 | 97% | 0.1/99.9 |
| " | 20.1 | 12.1 | 160.4-161.0 | 98% | |
| " | 19.6 | nd | 164.0-164.6 | 92% | |
| " | 11.9 | 13.2 | 161.8-162.6 | 94% | |
| " | 4.1 | 12 | 164.0-164.6 | 88% | 0.1/99.9 |
| Resolution ML | 13.9 | 13 | 159.2-159.6 | 62% | |
| " | 11.0 | 12.3 | 162.4-163.0 | 87% | |
| Combined ML & Salt | 19.9 | 13 | 162.6-163.4 | 85% | |
| TCI Americas Lot# FHG01 | | | 165.6-166.4 | | 0.1/99.9 |

FIG. 19

| Solvent | Temp °C | Sample weight g | Sample Volume mL | Wt% CPTA in Solution |
|---|---|---|---|---|
| 1,2-Dichloroethane | 41 | 0.1558 | 25.00 | 32.3 |
| | 35 | 0.1360 | 25.00 | 27.6 |
| | 25 | 0.1455 | 10.00 | 18.8 |
| | 20 | 0.0489 | 25.00 | 15.3 |
| | 20 | 0.0505 | 10.00 | 14.0 |
| | 16 | 0.3230 | 25.00 | 11.0 |
| | 2.1 | 0.1300 | 10.00 | 6.05 |
| Heptane | 56 | 0.4641 | 25.00 | 3.39 |
| | 45 | 0.3331 | 25.00 | 2.11 |
| | 35 | 0.3823 | 25.00 | 0.767 |
| | 25 | 0.6750 | 25.00 | 0.413 |
| | 20 | 0.1994 | 10.00 | 0.17 |
| | 2.1 | 0.6038 | 25.00 | 0.057 |

FIG. 20

| pH | Temp °C | Sample weight g | Sample Volume mL | Wt% CPTA in Solution |
|---|---|---|---|---|
| 9.4 | 35 | 0.3036 | 25.00 | 11.86 |
| 9.7 | 47 | 0.1111 | 25.00 | 18.28 |
| 9.5 | 19 | 0.2290 | 25.00 | 8.33 |
| 12.7 | 13.5 | 0.2012 | 25.00 | 4.89 |
| 12.6 | 25 | 0.3538 | 25.00 | 5.18 |
| 12.5 | 34 | 0.2320 | 25.00 | 7.30 |
| 12.5 | 42 | 0.3055 | 25.00 | 9.91 |

FIG. 21

| Wt Loaded g | | Reflux Time | pH | HPLC Area% | % CPTA | |
|---|---|---|---|---|---|---|
| (+)-Halofenate | 50% NaOH | | | (+)/(-) | Assay | Isolated |
| 8.65 | 1.67 (1 eq) | 0 h | 11.2 | 71.9/15.1 | | |
| | | 2 | | 78.3/17.2 | | |
| | | 5.5 | | 80.6/12.4 | | |
| | | 22.5 | 9.4 | 84.1/13.4 | | |
| | | Oil | | 80.3/19.6 | 92% | 81% |
| 6.94 | 2.68 (2 eq) | 0 | 12.6 | 83.4/11.3 | | |
| | | 1 | | 56.8/40.4 | | |
| | | 3.5 | | 49.0/45.0 | | |
| | | 20.5 | 11.6 | 47.5/45.0 | | |
| | | Oil | | 48.7/51.0 | 103% | 94% |
| 7.28 | 4.21 (3 eq) | 0 | 12.8 | 80.4/10.5 | | |
| | | 1.5 | 12.6 | 49.6/47.0 | | |
| | | Oil | | 47.3/52.5 | 102% | 88% |

RESOLUTION OF α-(PHENOXY)PHENYLACETIC ACID DERIVATIVES

This application claims the benefit of U.S. Provisional Application No. 60/608,927 filed Jun. 20, 2003.

FIELD OF THE INVENTION

The present invention relates to an enantioselective resolution process for the separation of α-(phenoxy)phenylacetic acids from its enantiomeric mixture.

BACKGROUND OF THE INVENTION

Esters and amides derivatives of α-(phenoxy)phenylacetic acids, such as halofenate, are chiral compounds and are useful in ameliorating a variety of physiological conditions, including conditions associated with blood lipid deposition, e.g., Type II diabetes and hyperlipidema. See, for example, U.S. Pat. Nos. 3,517,050 and 6,262,118. α-(phenoxy)phenylacetic acids contain a single chiral center at an asymmetrically substituted carbon atom alpha to the carbonyl carbon atom, and therefore exist in two enantiomeric forms.

Cytochrome P450 2C9 is an enzyme known to play a significant role in the metabolism of specific drugs. It is known to one skilled in the art that changes in drug metabolism mediated by inhibition of cytochrome P450 enzymes has a high potential to precipitate significant adverse effects in patients. It is also known that a racemic α-(phenoxy) phenylacetic acid, e.g., halofenic acid, inhibits cytochrome P450 2C9. See, for example, U.S. Pat. No. 6,262,118. Thus, administration of a racemic α-(phenoxy)phenyl-acetic acid, such as halofenic acid or its derivatives, can lead to a variety of drug interaction problems with other drugs, including anticoagulants, anti-inflammatory agents and other drugs that are metabolized by this enzyme. It has been found that the (−)-enantiomer of halofenic acid is about twenty-fold less active in its ability to inhibit cytochrome P450 2C9 compared to the (+)-enantiomer. Id. Thus, it is desirable to administer the (−)-enantiomer of halofenic acid or its derivatives which is substantially free of the (+)-enantiomer to reduce the possibility of drug interactions.

Therefore, there is a need for an efficient process for producing a product enriched in a desired enantiomer of a α-(phenoxy)phenylacidic acid, e.g., (−)-halofenic acid.

SUMMARY OF THE INVENTION

One aspect of the present invention provides a method for producing an enantiomerically enriched α-(phenoxy)phenylacetic acid compound of the formula:

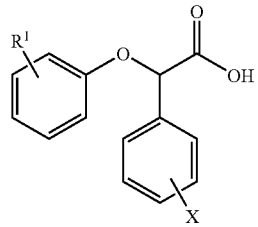

wherein
R$^1$ is alkyl or haloalkyl, and
X is halide;

from an enantiomeric mixture of the α-(phenoxy)phenylacetic acid compound comprising a first and a second enantiomers. In one particular embodiment, the enantiomeric mixture is a racemic mixture.

Methods of the present invention includes:
(a) producing a solution comprising a solid enantiomerically enriched acid-base salt of the first enantiomer by contacting the enantiomeric mixture of the α-(phenoxy)phenylacetic acid compound with less than 0.5 molar equivalents of an enantiomerically enriched chiral amine compound under conditions sufficient to produce the ratio of the amount of free first enantiomer to the amount of the free second enantiomer in the solution is about 1 to 3; and
(b) separating the solid acid-base salt of the first enantiomer from the solution at a temperature where the concentration of an acid-base salt of the second enantiomer of the α-(phenoxy)phenylacetic acid compound is near or below its saturation point.

At least a portion of the second enantiomer can be converted to the first enantiomer, e.g., racemized, by contacting the second enantiomer with a base. The resulting enatiomeric mixture can then be recycled and subjected to a similar enantiomeric enrichment process to increase the yield of the first enantiomer acid-base salt.

In one particular embodiment, the chiral amine compound is of the formula:

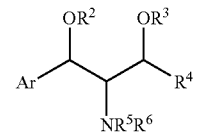

wherein
each of R$^2$ and R$^3$ is independently hydrogen or alkyl; or R$^2$ and R$^3$ together with atoms to which they are attached to form a heterocyclic ring moiety;
R$^4$ is hydrogen or alkyl;
each of R$^5$ and R$^6$ is independently hydrogen or alkyl, or one of R$^5$ or R$^6$ is an amine protecting group; and
Ar is aryl.

BRIEF DESCRIPTION OF THE DRAWINGS

FIG. 2 shows results of a process for resolving a racemic mixture of CPTA using CAF D-Base under a variety of crystallization conditions.

FIG. 6 is a table showing comparison of the model prediction to experimental results for entry 4 of FIG. 2.

FIG. 10A shows tables showing experimental data and a solubility model calculation for FIG. 7 (i.e., entry 13 of FIG. 2).

FIG. 10B is a table showing experimental data and a solubility model calculation for entry 4 of FIG. 2 at 28.3° C.

FIG. 13 is a table of results in Example 24 showing yield of CPTA resolution using CAF D-Base under variety of crystallization conditions.

FIG. 14 shows a cooling profiles for the resolution crystallization of various entries in FIG. 2.

FIG. 15 is a table showing the amount of (−)-halofenate yield from (−)-CPTA salt in Example 26.

FIG. 18 is a table showing the results of CAF D-Base recovery at various pH as described in Example 30.

FIG. 19 is experimental results of solubility determination of racemic CPTA in 1,2-dichloroethane and heptane as determined in Example 33.

FIG. 20 is experimental results of solubility determination of racemic CPTA sodium salt in water as determined in Example 41.

FIG. 21 is experimental results of basic hydrolysis of (+)-halofenate as determined in Example 42.

DETAILED DESCRIPTION

I. Definitions

Figure 1:
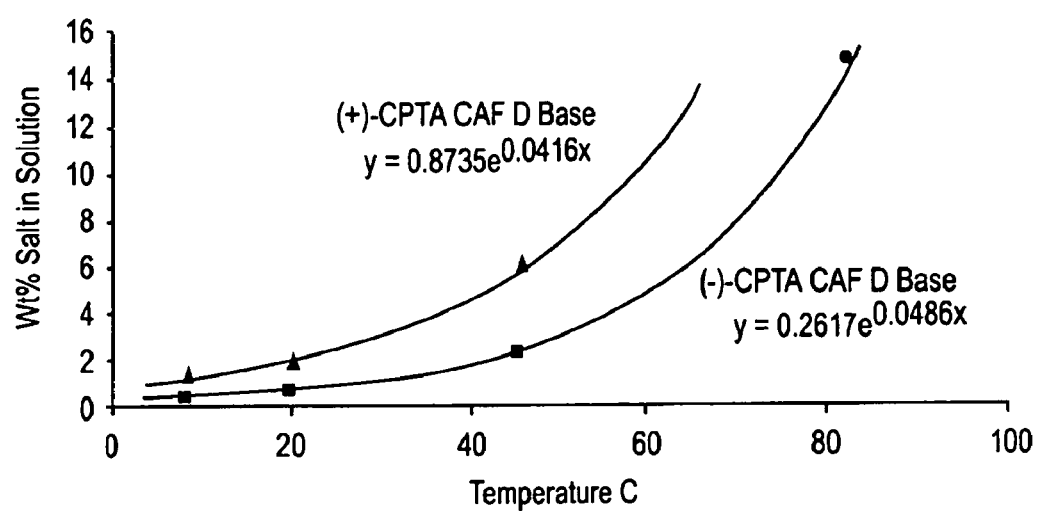
FIG. 1 is a graph showing the solubility profiles of (−)- and (+)-CPTA/CAF D-Base salts in 2-propanol.

"Alkyl" refers to straight or branched aliphatic hydrocarbons chain groups of one to ten carbon atoms, preferably one to six carbon atoms, and more preferably one to four carbon atoms. Exemplary alkyl groups include, but are not limited to, methyl, ethyl, n-propyl, 2-propyl, tert-butyl, pentyl, and the like.

"Aryl" refers to a monovalent monocyclic or bicyclic aromatic hydrocarbon moiety of 6 to 10 carbon ring atoms. Unless stated or indicated otherwise, an aryl group can be substituted with one or more substituents, preferably one, two, or three substituents, and more preferably one or two substituents selected from alkyl, haloalkyl, nitro, and halo. More specifically the term aryl includes, but is not limited to, phenyl, 1-naphthyl, and 2-naphthyl, and the like, each of which is optionally substituted with one or more substituent(s) discussed above.

"CAF D base" refers to chloramphenicol D base, i.e., D-threo-(−)-2-amino-1-(nitrophenyl)-1,3-propanediol.

"Chiral" or "chiral center" refers to a carbon atom having four different substituents. However, the ultimate criterion of chirality is non-superimposability of mirror images.

The terms "CPTA" and "halofenic acid" are used interchangeably herein and refer to (4-chlorophenyl)(3-trifluoromethylphenoxy)acetic acid.

"Enantiomeric mixture" means a chiral compound having a mixture of enantiomers, including a racemic mixture. Preferably, enantiomeric mixture refers to a chiral compound having a substantially equal amounts of each enantiomers. More preferably, enantiomeric mixture refers to a racemic mixture where each enantiomer is present in an equal amount.

"Enantiomerically enriched" refers to a composition where one enantiomer is present in a higher amount than prior to being subjected to a separation process.

"Enantiomeric excess" or "% ee" refers to the amount of difference between the first enantiomer and the second enantiomer. Enantiomeric excess is defined by the equation: % ee=(% of the first enantiomer)−(% of the second enantiomer). Thus, if a composition comprises 98% of the first enantiomer and 2% of the second enantiomer, the enantiomeric excess of the first enantiomer is 98%−2% or 96%.

The terms "halide" and "halo" are used interchangeably herein and refer to halogen, which includes F, Cl, Br, and I, as well as pseudohalides, such as —CN and —SCN.

"Haloalkyl" refers to alkyl group as defined herein in which one or more hydrogen atoms have been replaced with halogens, including perhaloalkyls, such as trifluoromethyl.

"Halofenate" refers to 2-acetamidoethyl 4-chlorophenyl-(3-trifluoromethyl-phenoxy)acetate (i.e., 4-chloro-α-(3-(trifluoromethyl)phenoxy)benzeneacetic acid, 2-(acetylamino) ethyl ester or (4-chlorophenyl)(3-trifluoromethylphenoxy) acetic acid), 2-(acetylamino)ethyl ester).

"Heteroalkyl" means a branched or unbranched acyclic saturated alkyl moiety containing one or more heteroatoms or one or more heteroatom-containing substituents, where the heteroatom is O, N, or S. Exemplary heteroatom-containing substituents include =O, —OR$^a$, —C(=O)R$^a$, —NR$^a$R$^b$, —N(R$^a$)C(=O)R$^b$, —C(=O)NR$^a$R$^b$ and —S(O)$_n$ R$^a$ (where n is an integer from 0 to 2). Each of R$^a$ and R$^b$ is independently hydrogen, alkyl, haloalkyl, aryl, or aralkyl. Representative examples of heteroalkyl include, for example, N-acetyl 2-aminoethyl (i.e., —CH$_2$CH$_2$NHC (=O)CH$_3$).

The terms "heterocyclyl" and "heterocyclic ring" are used interchangeably and refer to a non-aromatic cyclic moiety of 3 to 8 ring atoms in which one, two, or three ring atoms are heteroatoms selected from N, O, or S(O)$_n$ (where n is an integer from 0 to 2), the remaining ring atoms being C, where one or two C atoms may optionally be replaced by a carbonyl group. Unless stated or indicated otherwise, the heterocyclyl ring can be optionally substituted independently with one, two, or three substituents selected from halogen, alkyl, aryl, hydroxy, amino, or alkoxy. More specifically the term heterocyclyl includes, but is not limited to, 1,3-dioxane and its derivatives, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

The term "metal" includes Group I, II, and transition metals as well as main grouop metals, such as B and Si.

"Optical purity" refers to the amount of a particular enantiomer present in the composition. For example, if a composition comprises 98% of the first enantiomer and 2% of the second enantiomer, the optical purity of the first enantiomer is 98%.

Unless otherwise stated, the term "phenyl" refers to an optionally substituted phenyl group. Suitable phenyl substituents are same as those described in the definition of "aryl." Similarly, the term "phenoxy" refers to a moiety of the formula —OAr$^a$, wherein Ar$^a$ is phenyl as defined herein. Thus, the term "α-(phenoxy)phenylacetic acid"

refers to acetic acid that is substituted on the 2-position with an optionally substituted phenyl and optionally substituted phenoxy moieties.

"Protecting group" refers to a moiety that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilylethanesulfonyl (SES), trityl and substituted trityl groups, allyloxycarbonyl, 9-fluorenylmethyloxycarbonyl (FMOC), nitro-veratryloxycarbonyl (NVOC), and the like.

The term "rate" when referring to a formation of a salt refers to kinetic and/or thermodynamic rates.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or (l) meaning that the compound is "levorotatory" and with (+) or (d) is meaning that the compound is "dextrorotatory". There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. See, e.g., Streitwiesser, A. & Heathcock, C. H., INTRODUCTION TO ORGANIC CHEMISTRY, 2$^{nd}$ Edition, Chapter 7 (MacMillan Publishing Co., U.S.A. 1981).

The terms "substantially free of its (+)-stereoisomer," "substantially free of its (+)-enantiomer," are used interchangeably herein and mean that the compositions contain a substantially greater proportion of the (−)-isomer in relation to the (+)-isomer. In a preferred embodiment, the term "substantially free of its (+) stereoisomer" means that the composition is at least 90% by weight of the (−)-isomer and 10% by weight or less of the (+)-isomer. In a more preferred embodiment, the term "substantially free of its (+)-stereoisomer" means that the composition contains at least 99% by weight of the (−)-isomer and 1% by weight or less of the (+)-isomer. In the most preferred embodiment, the term "substantially free of its (+)-stereoisomer" means that the composition contains greater than 99% by weight of the (−)-isomer. These percentages are based upon the total amount of isomers in the composition.

II. Introduction

While chiral synthesis has made an extensive progress in recent years, resolution of racemates still remains the method of choice in industrial process for preparation of optically active, i.e., chiral, compounds. Typically, a chiral compound is synthesized in a racemic form and the final product is resolved to yield an enantiomerically enriched compound.

This process of resolving the final product is particularly useful in a large scale preparation of pharmaceutically active chiral compounds. Although enantiomers of a chiral compound have exact same chemical bonds, the spatial orientation of atoms in enantiomers is different. Thus, one enantiomer of a chiral drug often exerts desired activity with a significantly less side-effect(s) than the other enantiomer. While such relationship between chirality of an optically active drug and its side-effect(s) has been known for sometime, many chiral drugs are still administered in a racemic form.

Diastereomeric crystallization is widely used on industrial scale. The theoretical once-through yield of a resolution via diastereomer crystallization is 50 percent. Typically, however, more than one re-crystallization process is necessary in order to produce a composition that is of a sufficient optical purity.

The present invention provides a method for enantiomerically enriching an enantiomeric mixture, preferably a racemic mixture, of α-(phenoxy)phenylacetic acid compound, e.g., halofenic acid. Preferably, methods of the present invention provides a solid acid-base salt of the (−)-enantiomer of α-(phenoxy)phenylacetic acid compound. In this manner, the (−)-enantiomer can be readily separated from the solution.

The carboxylic acid group of the enantiomerically enriched α-(phenoxy)phenylacetic acid can then be activated by a carboxylic acid activation group to produce an activated α-(phenoxy)phenylacetic acid, which can be reacted with an alcohol, an amine, a thiol, or other nucleophilic compounds to produce an enantiomerically enriched α-(phenoxy)phenylacetic acid esters, amides, thioesters, or other derivatives, respectively. Thus, enantiomerically enriched α-(phenoxy)phenylacetic acid compounds produced using methods of the present invention are useful in producing α-(phenoxy)phenylacetic acid derivatives such as those disclosed in U.S. Pat. No. 3,517,050. In particular, methods of the present invention are useful in producing (−)-halofenate.

III. Enantioselective Crystallization

As noted above, most enantioselective crystallization processes require more than one re-crystallization process in order to produce a composition that is of a sufficient optical purity. However, present inventors have found that under certain conditions disclosed herein, α-(phenoxy)phenylacetic acid compound of a sufficient optical purity can be produced by a single crystallization process. Thus, in one aspect, methods of the present invention are based on the surprising and unexpected discovery by the present inventors that an enantiomeric mixture of a α-(phenoxy)phenylacetic acid compound can be enantiomerically enriched using a chiral amine compound. In particular, methods of the present invention provide a desired enantiomer of the α-(phenoxy)phenylacetic acid compound in optical purity of at least about 90%, preferably at least about 95%, more preferably at least about 97%, and most preferably at least about 98%.

In one embodiment, methods of the present invention provide enantiomeric enrichment of an enantiomeric mixture, preferably a racemic mixture, of a α-(phenoxy)phenylacetic acid compound of the formula:

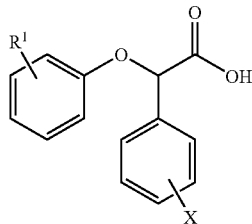

I wherein $R^1$ is alkyl or haloalkyl, and X is halide. The process generally involves forming a solid enantiomerically enriched acid-base salt of the α-(phenoxy)phenylacetic acid compound uing a chiral amine compound.

In particular, methods of the present invention are directed to the resolution of α-(phenoxy)phenylacetate acid, e.g., halofenic acid (where $R^1$ is $CF_3$ and X is Cl), of the formula:

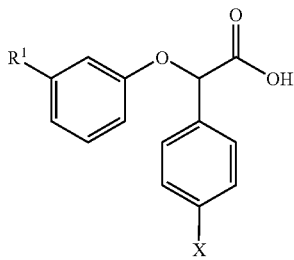

II wherein $R^1$ is alkyl or haloalkyl, and X is halide.

In one particular embodiment, methods of the present invention are directed to the resolution of α-(phenoxy) phenylacetate acid of Formula I or, preferably of Formula II, where X is chloro.

Yet in another embodiment, methods of the present invention are directed to the resolution of α-(phenoxy)phenylacetic acid of Formula I or, preferably, Formula II, where $R^1$ is haloalkyl, preferably trifluoromethyl.

In one particular embodiment, α-(phenoxy)phenylacetic acid is crystallized using a chiral base. A wide variety of chiral bases can be used, including those disclosed in the Examples section below. Preferably, the chiral base used results in a solid acid-base salt of the (−)-enantiomer of α-(phenoxy)phenylacetic acid. In this manner, the (−)-enantiomer is readily separated from the solution, for example, by filtration. In one particular embodiment, the chiral base is an amine compound of the formula:

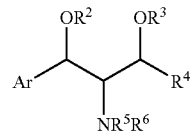

III wherein each of $R^2$ and $R^3$ is independently hydrogen, alkyl or a hydroxy protecting group; or $R^2$ and $R^3$ together with atoms to which they are attached to form a heterocyclic ring moiety; $R^4$ is hydrogen or alkyl; each of $R^5$ and $R^6$ is independently hydrogen or alkyl, or one of $R^5$ or $R^6$ is an amine protecting group; and Ar is aryl.

In one particular embodiment, $R^2$ and $R^3$ together along with oxygen atoms to which they are attached to form 1,3-dioxane, a substituted 1,3-dioxane (e.g., dialkyl substituted 1,3-dioxane, such as 5,5-dimethyl-1,3-dioxane), or a derivative thereof.

In another embodiment, $R^2$ and $R^3$ are hydrogen.

Yet in another embodiment, $R^4$ is hydrogen.

In still another embodiment, Ar is a substituted aryl. A particularly preferred Ar moiety is optionally substituted phenyl. An especially preferred Ar moiety is 4-nitrophenyl.

Still further, combinations of the preferred groups described above will form other preferred embodiments. For example, one particularly preferred chiral base is an amine compound of Formula III above, wherein $R^2$, $R^3$, $R^4$, $R^5$ and $R^6$ are hydrogen; and Ar is 4-nitrophenyl. And a particularly preferred α-(phenoxy)phenylacetic acid compound is of Formula II above, wherein $R^1$ is trifluoromethyl and X is chloro. In this manner, a wide variety of preferred chiral bases and α-(phenoxy)phenylacetic acid compounds are embodied within the present invention.

The present inventors have found that the amount of chiral base used in crystallization of the α-(phenoxy)phenylacetic acid has a significant effect on the optical purity of the enantiomeric enrichment. For example, when a chiral amine compound of the formula:

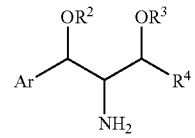

(wherein $R^2$, $R^3$, $R^4$ and Ar are those defined herein) is used in crystallization of the α-(phenoxy)phenylacetic acid compound, higher % ee obtained by using the chiral amine compound in an amount less than 0.5 molar equivalent, preferably about 0.48 molar equivalent or less, more preferably about 0.47 molar equivalent or less, and most preferably about 0.45 molar equivalent or less. It should be recognized that the chiral amine compound itself should be of a sufficient enantiomeric purity in order to yield a highly enantiomerically enriched α-(phenoxy)phenylacetic acid derivatives.

The crystallization is typically conducted in a solvent that allows a different solubility of salts that are formed between two enantiomers of the α-(phenoxy)phenylacetic acid and the chiral amine. In this manner, one of the diastereomeric salt precipitates out of the solution preferentially. Suitable crystallization solvents include protic solvents, such as alcohols. A particularly preferred crystallization solvent is isopropyl alcohol.

The yield of enantiomerically enriched α-(phenoxy)phenylacetic acid also depends on, among others, the amount of crystallization solvent used. For example, if a large quantity of crystallization solvent is used, the mixture becomes too dilute and the solid formation is reduced. If the amount of crystallization solvent used is too small, the solution will be supersaturated with the undesired diastereomeric salt which may lead to crystallization of the undesired diastereomeric salt, thereby reducing the optical purity of a desired enantiomer. Thus, when isopropanol is used as the crystallization solvent, the amount of crystallization solvent used is preferably from about 2 grams to about 6 grams per one gram of the α-(phenoxy)phenylacetic acid compound, more preferably from about 3 grams to about 5 grams, still more preferably from about 3.5 grams to about 4.5 grams, and most preferably about 4 grams.

In one embodiment, the crystallization process involves heating the crystallization solution mixture to a temperature above the nucleation temperature of both enantiomers to dissolve substantially all of both enantiomers. For example, the crystallization solution is heated to a temperature in the range of from about 60° C. to the boiling point of the solution, preferably from about 70° C. to about 80° C. More preferably, the crystallization solution is heated to about 75° C. The solution can be heated prior to and/or after the chiral amine compound is added. Heating is carried out until the solid materials are substantially completely dissolved, which typically ranges from about 0.5 to about 16 hours, preferably from about 1 to about 8 hours.

The crystallization solution is then cooled until it is at or below the nucleation temperature of the first diastereomeric salt, e.g., salt of (−)-enantiomer of the α-(phenoxy)-phenylacetic acid, but preferably above the nucleation temperature of the second diastereomeric salt, e.g., salt of (+)-enantiomer of the α-(phenoxy)phenylacetic acid. This allows formation of a solid acid-base salt of the first enantiomer with the chiral amine compound. Without being bound by any theory, it is believed that the use of a chiral amine compound results in formation of an acid-base salt with one of the enantiomer at a significantly faster rate than formation of an acid-base salt of the other enantiomer. This rate may be due to kinetic and/or thermodynamic rate difference between the two enantiomers. As with a typical compound, the solubility profile of the α-(phenoxy)phenylacetic acid compound of the present invention has a higher solubility at a higher temperature. Therefore, by cooling the crystallization solution to just above the nucleation temperature of the second diastereomeric salt affords a higher recovery yield of the solid first diastereomeric salt.

After the slurry is formed, the crystallization solution can be further cooled until the temperature of the solution is near or above the saturation point of the second diastereomeric salt. This prevents formation of a diastereomeric solid acid-base salt from the second enantiomer while increasing the formation of the diastereomeric solid acid-base salt of the first enantiomer.

The rate of cooling the crystallization solution may affect the optical purity of the solid acid-base salt that is formed. For example, if the crystallization solution is cooled too fast, the undesirable enantiomer may get trapped within the lattice of the solid acid-base salt of the desired enantiomer. However, a too slow cooling rate increases the production time and cost. Therefore, the crystallization solution should be cooled at a rate which minimizes the loss of optical impurity but at a rate sufficient to be economical. Typically, the crystallization solution cooling rate is from about 0.05° C./min to about 1° C./min, preferably from about 0.1° C./min to about 0.7° C./min, and more preferably from about 0.25° C./min to about 0.4° C. The crystallization solution is then maintained at above the saturation point of the solid acid-base salt of the second, i.e., undesired, enantiomer. Typically, the crystallization solution is maintained at this temperature for about 1 to about 72 hours, preferably from about 2 to about 48 hours, and more preferably from about 3 to about 30 hours.

As expected, using a small amount of chiral amine compound allows selective formation of the solid acid-base salt of the first enantiomer. However, the resulting yield will correspondingly be small. Theoretically, the amount of yield of the desired enantiomer from a racemic mixture is 50%. Thus, if 0.5 molar equivalent of the chiral amine compound is used, the theoretical yield is 50% of the total α-(phenoxy)phenylacetic acid (or 100% of the desired enantiomer). In order to be economically desirable, methods of the present invention provide at least about 50% yield of the desired enantiomer, preferably at least about 60%, more preferably at least about 70%, and most preferably at least about 75%. Assuming 100% selectivity, these yields correspond to adding about 0.25, 0.30, 0.35 and 0.375 molar equivalent of the chiral amine compound, which represent a minimum amount of the chiral amine compound that need to be added to the crystallization solution.

It is believed that the tendency for the second enantiomer to form a solid acid-base salt with the chiral amine compound is one of the major causes for variability of conventional crystallization processes. Thus, by determining the supersaturation point of the second, i.e., undesired, enantiomer, one can minimize or prevent unpredictability of a solid acid-base formation of the second enantiomer. Supersaturation points can be readily determined by one skilled in the art, e.g., by a solubility experiment.

It should be noted that while methods of the present invention are discussed in reference to the enrichment of (−)-enantiomer that is present in the racemic mixtures, methods of the present invention are also applicable for enriching the (+)-enantiomer. The method of the present invention essentially provides a solid precipitate enriched in the (−)-enantiomer and a liquid filtrate, i.e., mother liquor, enriched in the (+)-enantiomer. Liberation of the desired (−)-enantiomer and recovery of the chiral amine compound from the precipitated salt can be readily accomplished by acidification of the salt with, for example, a dilute mineral acid or any other inorganic or organic acid conventionally known to hydrolyze salts of this nature. While this procedure leaves the filtrate as an undesired by-product, the filtrate can be further treated with acid or, preferably, base to convert the (+)-enantiomer enriched filtrate to the racemic mixture. For example, the (+)-enantiomer can be racemized using aqueous sodium hydroxide solution. This racemic mixture can then be reused, i.e., recycled. In addition, the chiral amine compound can also be recovered from the above described conversion step and recycled. Thus, the process of the present invention lends itself readily to a recycling-type of procedure.

IV. Synthesis of Racemic α-(phenoxy)phenylacetic acid

One method of producing a racemic mixture of α-(phenoxy)phenylacetic acid of Formula I is shown in Scheme I below.

Scheme I

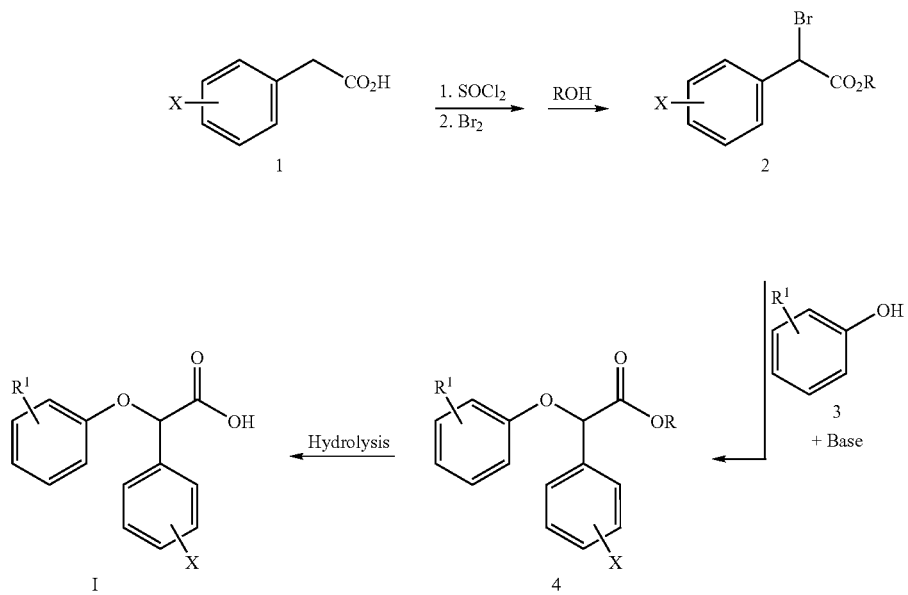

Thus, conversion of phenylacetic acid 1 to an activated carboxylic acid derivative, e.g, acid chloride, followed by α-bromination gave α-bromophenylacetyl chloride (not shown). The acid chloride was then converted to ester 2, where R is typically alkyl. Preferably, alcohol ROH, which is used to convert the acid chloride to ester 2, is the same alcohol that is used as a solvent in a subsequent reaction. In this manner, the number of different solvent types is minimized. In addition, by using the same ROH as the solvent in the subsequent reaction, the amount of by-product, e.g., by trans-esterification, formation is minimized. For example, isopropyl ester 2, i.e., where R is isopropyl, is particularly advantages as the subsequent reaction is conveniently carried out in isopropanol solvent. A displacement reaction of ester 2 with a phenol compound 3 in the presence of a base, such as a hydroxide (e.g., potassium hydroxide), gave a α-(phenoxy)phenylacetic acid ester 4. Hydrolysis of α-(phenoxy)phenylacetic acid ester 4 afforded α-(phenoxy)phenylacetic acid I.

In this manner, (4-chlorophenyl)-(3-trifluoromethylphenoxy)-acetic acid, i.e., CPTA, can be prepared in five steps without intermediate isolation in about 85% yield following crystallization from heptane.

V. Utility of Enantiomerically Enriched α-(phenoxy)phenylacetic acid

Enantiomerically enriched α-(phenoxy)phenylacetic acid compounds are useful intermediates in preparing a variety of pharmaceutically active compounds, including α-(phenoxy)phenylacetic acid compounds disclosed in U.S. Pat. No. 3,517,050. Thus, anther aspect of the present invention provides a method for enantioselectively producing a α-(phenoxy)phenylacetate compound of the formula:

IV from a racemic mixture of a α-(phenoxy)phenylacetic acid compound Formula I, wherein $R^1$ is alkyl or haloalkyl, X is halide and $R^7$ is heteroalkyl, preferably N-acetyl 2-aminoethyl (i.e., a moiety of the formula —$CH_2CH_2NHC(=O)CH_3$). The method involves resolving the racemic mixture of the α-(phenoxy)phenylacetic acid compound of Formula I as described above and producing an enantiomerically enriched activated α-(phenoxy)phenylacetic acid by reacting the enantiomerically enriched α-(phenoxy)phenylacetic acid with a carboxylic acid activating reagent. Suitable carboxylic acid activating reagents include thionyl halides (e.g., thionyl chloride), anhydrides, thioester generating reagents, and other carboxylic acid activating reagents known to one skilled in the art.

The activated α-(phenoxy)phenylacetic acid is than reacted with a compound of the formula $(R^7—O)_wM$, e.g., N-acetyl ethanolamine derivative, to produce enantiomerically enriched α-(phenoxy)phenylacetate compound of Formula III, where $R^7$ is as defined above, M is hydrogen or a metal, e.g., Na, K, Li, Ca, Mg, Cs, etc. and the superscript w is the oxidation state of M. The present inventors have discovered that the reaction between the activated acid and the compound of formula $(R^7—O)_wM$ can be carried out without any significant racemization.

Additional objects, advantages, and novel features of this invention will become apparent to those skilled in the art upon examination of the following examples thereof, which are not intended to be limiting.

EXAMPLES

Reagents and Experimental Setup

Unless otherwise stated, reagents and solvents were purchased from Aldrich Chemical or Fisher Scientific. N-Acetylethanolamine was also obtained from Lancaster Synthesis. The racemic CPTA, i.e., halofenic acid was prepared according to the procedures disclosed in U.S. Pat. Nos. 3,517,050 and 6,262,118 all of which are incorporated herein by reference in their entirety. (1R,2R)-(−)-2-Amino-1-(4-nitrophenyl)-1,3-propandiol (i.e., CAF D-Base) was obtained from TCI Americas.

Operations were conducted under a positive nitrogen atmosphere. A Camile process control computer attached to a recirculating heating and cooling system was used to regulate jacket temperatures in the jacketed straight-walled bottom-drain glass reactors. Unless otherwise indicated, solvents were removed using a Buchi rotary evaporator at 15 to 25 torr with a bath temperature of up to 40° C. Solid samples were dried in a vacuum oven at 40° C., 15 to 25 torr. A Cenco HYVAC vacuum pump was used to supply vacuum of less than 1 torr for vacuum distillations. Water levels were determined by Karl Fisher analysis using a Metrohm 756 KF Coulometer and HYDRANAL Coulomat AG reagent. Melting points were determined using a Mettler Toledo FP62 melting point apparatus. pH was measured using a calibrated Orion Model 290A pH meter. Proton and $^{13}C$ NMR spectra were recorded on a Bruker Avance 300 MHz spectrometer.

Chiral HPLC analysis was carried out at λ=240 nm by injecting 10 μL of sample dissolved in mobile phase onto a (R,R)WHELK-O 1.5 μm 250×4.6 mm column (Regis Technologies) and eluting with a 1.0 mL/min flow of 95/5/0.4 (v/v/v) hexanes/2-propanol/acetic acid. For solid samples of the CPTA/CAF D-Base diastereomeric salt, the solid was added to aqueous hydrochloric acid and the CPTA was extracted into methylene chloride; after removing the solvent from the methylene chloride layer, the residue was dissolved in mobile phase for analysis.

Achiral HPLC analysis was carried out at λ=220 nm by injecting 5 μL of sample dissolved in mobile phase onto a Phenomenex LUNA 5 μm C18(2) 250×4.6 mm column at 25° C. A 1.5 ml/min flow of the gradient starting at 66 vol % water/34 vol % acetonitrile/0.1 vol % trifluoroacetic acid and increasing linearly to 26 vol % water/74 vol % acetonitrile/0.1 vol % trifluoroacetic acid at 20 minutes was used.

For analysis of acidic solutions of esters, such as halofenate, acetonitrile was used as the injection solvent. When determined, product concentrations for CPTA and halofenate were evaluated by HPLC assay using the external standard method and the achiral analysis procedure at sample concentrations of less than 2.5 mg/mL.

Example 1

Previous resolution of CPTA has been reported in U.S. Pat. No. 3,517,050, in which cinchonidine was used as the chiral base, and the (+)-enantiomer of CPTA precipitated as the diastereomeric salt. One major drawback to this procedure was that the desired (−)-enantiomer remained in the mother liquor, making separation of a pure (−)-enantiomer fraction difficult.

This example shows the results of resolving a racemic mixture of CPTA using a variety of different chiral bases to obtain a solid enantiomerically enriched (−)-isomer. Unlike the previous method, methods of the present invention allow the solid enantiomerically enriched (−)-CPTA to be readily isolated from the solution.

Racemic CPTA was prepared by the potassium hydroxide hydrolysis of racemic halofenate. For chiral base screening, equal molar mixtures of CPTA and the chiral base were mixed in ethanol, methanol and acetone in glass vials, and the solutions were allowed to stand undisturbed. After holding overnight at ambient temperature, the samples that remained in solution were placed in a refrigerator at 5° C. After holding overnight in the refrigerator, a small amount of water was added to the samples that remained a solution in ethanol. After four days at ambient temperature, the aqueous ethanol solutions were placed back in the refrigerator. All of the samples remained in the refrigerator, and were periodically checked for precipitate formation over the course of a month. A list of the bases and solvent conditions examined, and temperatures at which crystalline salts were found is shown in Table 1.

TABLE 1

Bases Examined for CPTA Resolution.

| Base | Solvent System | | | |
|---|---|---|---|---|
| | EtOH | EtOH (aq) | Acetone | MeOH |
| S-(−)-Methylbenzylamine | E | E | E | E |
| Quinine | C (22° C.) | | C (22° C.) | C (22° C.) |
| Quinidine | | | E | E |
| L-Tyrosine Hydrazide | | | C (22° C.) | |
| L-Leucine Methyl Ester Hydrochloride* | | | E | E |
| l-2-Amino-1-butanol | E | E | E | E |
| Brucine | E | E | E | E |
| (S)-(+)-2-Pyrrolidine-methanol | E | E | E | E |
| (S)-(+)-2-Amino-3-methyl-1-butanol | | | | E |
| (S)-(+)-2-Amino-1-propanol | | | | E |
| (S)-(−)-2-Amino-3-phenyl-1-propanol | | | | E |
| (1S,2S)-(+)-Pseudoephedrine | E | E | E | E |
| (1S,2S)-(+)-2-Amino-1-phenyl-1,3-propanediol | E | E | E | E |
| (1S,2S)-(+)-2-Amino-1-(4-nitrophenyl)-1,3-propanediol | C (5° C.) | | | |
| (1R,2S)-(−)-Norephedrine | E | E | E | E |

TABLE 1-continued

Bases Examined for CPTA Resolution.

| | Solvent System | | | |
|---|---|---|---|---|
| Base | EtOH | EtOH (aq) | Acetone | MeOH |
| (1R,2S)-(−)-Ephedrine | | | | E |
| (1R,2R)-(−)-2-Amino-1-(4-nitrophenyl)-1,3-propandiol | C (22° C.) | | | |
| (+)-Cinchonone | E | E | E | E |
| (−)-Cinchonidine | C (22° C.) | | | |
| (−)-Strychnine | E | E | E | E |

E—Evaluated
C—Crystallized at (Temperature)
*With 1 mol/mol of Aqueous Sodium Hydroxide Four chiral bases, quinine, L-tyrosine hydrazide, (−)-cinchonidine, and both enantiomers of 2-amino-1-(4-nitrophenyl)-1,3-propandiol, were found to give crystalline salts from racemic CPTA. For samples that crystallized, the solid was isolated by filtration, and both the solid phase and mother liquor were analyzed by chiral HPLC to determine the enantiomeric composition of both streams. The results from the screen are shown in Table 2. Three of the bases shown in Table 2 gave the (+)-enantiomer enrichment in the solid phase.

Example 2

This example shows the results of resolving CPTA with CAF D base in ethanol and 2-propanol.

The results for ethanol and 2-propanol are summarized in Table 3 below. For this evaluation, the slurries were sampled at various points in the cooling profile, and the enantiomeric composition of both the solid and solution phases determined. From this information, the % ee of the solid phase and expected weight percent yield (maximum 50% yield

TABLE 2

Results from Chiral Base Screen.

| | | | Solid | | Mother Liquor | | % Yield |
|---|---|---|---|---|---|---|---|
| Base | Solvent | Temp ° C. | % (+) | % (−) | % (+) | % (−) | Calculated |
| L-Tyrosine Hydrazide | Acetone | 22 | 86.6 | 13.4 | 40.7 | 59.3 | 20.3 |
| (−)-Cinchonidine | Ethanol | 22 | 66.8 | 33.2 | 12.0 | 88.0 | 69.3 |
| (1S,2S)-(+)-2-Amino-1-(4-nitrophenyl)-1,3-propandiol | Ethanol | 22 | 93.2 | 6.8 | 28.5 | 71.5 | 33.2 |
| Quinine | Ethanol | 22 | 39.9 | 60.1 | 60.1 | 39.9 | 50.1 |
| | Acetone | 22 | 28.2 | 71.8 | 58.9 | 41.1 | 28.9 |
| | Acetone* | 5 | 23.0 | 77.0 | 83.5 | 16.5 | 55.4 |
| | Methanol | 22 | 25.8 | 74.2 | 53.0 | 47.0 | 10.9 |
| | 2-Propanol | 30 | 43.2 | 56.8 | 64.3 | 35.7 | 67.6 |
| | 2-Propanol** | 30 | 40.4 | 59.6 | 78.8 | 21.1 | 75.0 |
| | 2-Propanol* | 21 | 42.3 | 57.7 | 59.1 | 40.9 | 53.9 |

*More Dilute
**Slower Cooling Profile

Included in Table 2 is the percent yield of solid calculated from the isomeric ratio in the solid and mother liquor streams. The equation used is shown below. The maximum theoretical yield with 100% isomeric purity is 50%. Yields over 50% indicate inclusion of the other isomer.

Equation to calculate yield from isomer ratios.

Set: a=area % Component 1 in starting material; b=area % Component 2 in starting material; x=area % Component 1 in isolated; y=area % Component 2 in isolated; w=area % Component 1 in mother liquor; z=area % Component 2 in mother liquor; E=g material isolated; F=g material in mother liquor.

And: $a+b=100\%$; $E+F=1$

Then: $xE+wF=a$; $yE+zF=b$

Solving: $xE+w(1-E)=a$; $yE+Z(1-E)=b$ $E$=isolated yield=$(a-w)/(x-w)=(b-z)/(y-z)$ with 100% ee), calculated from the isomer ratio, were determined. Included in Table 3 is the yield of (−)-CPTA, which is derived from the weight percent yield and the (−)-CPTA content of the solid phase (maximum 100% yield with 100% ee).

In this particular study, the best results in ethanol used 1 mole of CAF D Base per mole of CPTA. Approximately 72% yield of the (−)-CPTA CAF D Base salt was calculated from the chiral composition of both phases, with an 87.6% ee of the (−)-CPTA salt in the solid phase. Use of one molar equivalent of CAF D Base in 2-propanol at a similar concentration gave a lower resolution. Higher enantiomeric enrichment was achieved when 0.55 mole of CAF D Base per mole of CPTA was used. Under these conditions, approximately 76–79% yield of the (−)-CPTA CAF D Base salt was calculated from the phase compositions, with an 87–90% ee of (−)-CPTA in the solid phase. Calculated weight percent yields, which do not take into account physical losses, were 41 to 42%; actual weighed isolated yields were 37 to 39%.

using cinchonidine-resolved (+)-CPTA. As FIG. 1 shows, the desired (−)-CPTA diastereomer is approximately three times less soluble than the (+)-CPTA form. Equations

TABLE 3

Resolution of CPTA with CAF D Base.

| wt % CPTA | mole/mole base | T ° C. | Solid % (+) | Solid % (−) | M.L. % (+) | M.L. % (−) | % ee | % Yield 50% Max | % Yield (−)-CPTA |
|---|---|---|---|---|---|---|---|---|---|
| | | | | Ethanol | | | | | |
| 13.68 | 1.02 | 11 | 10.2 | 89.8 | 75.8 | 24.2 | 79.7 | 39.4 | 68.9 |
| | | 0 | 8.9 | 91.1 | 76.4 | 23.6 | 82.3 | 39.1 | 69.9 |
| | | −9 | 6.2 | 93.8 | 78.0 | 22.0 | 87.6 | 39.0 | 72.4 |
| 14.09 | 0.50 | 18 | 6.6 | 93.4 | 55.5 | 44.5 | 86.7 | 11.2 | 20.7 |
| | | −5 | 10.3 | 89.7 | 59.7 | 40.3 | 79.3 | 19.7 | 35.0 |
| | | | | 2-Propanol | | | | | |
| 15.72 | 1.01 | 12 | 45.9 | 54.1 | 66.9 | 33.1 | 8.2 | 80.4 | 85.8 |
| | | −8 | 46.6 | 53.4 | 68.0 | 32.0 | 6.7 | 84.2 | 87.1 |
| 16.6 | 0.50 | 36 | 8.3 | 91.7 | 69.6 | 30.4 | 83.5 | 32.0 | 58.6 |
| | | 22 | 10.2 | 89.8 | 73.9 | 26.1 | 79.6 | 37.5 | 62.3 |
| | | 2 | 8.0 | 92.0 | 74.9 | 25.1 | 84.0 | 37.2 | 68.5 |
| 16.7 | 0.55 | 49 | 26.3 | 73.7 | 64.5 | 35.5 | 47.4 | 38.0 | 56.1 |
| | | 50 | 7.5 | 92.5 | 63.3 | 36.7 | 85.0 | 23.8 | 44.0 |
| | | 20 | 6.7 | 93.3 | 79.7 | 20.3 | 86.6 | 40.7 | 75.6 |
| 16.7 | 0.55 | 50 | 8.8 | 91.2 | 64.2 | 35.8 | 82.3 | 25.6 | 46.6 |
| | | 35 | 9.1 | 90.9 | 69.0 | 31.0 | 81.7 | 31.7 | 57.6 |
| | | 6 | 5.2 | 94.8 | 75.0 | 25.0 | 89.6 | 35.8 | 67.9 |
| | | 5 | 5.7 | 94.3 | 81.9 | 18.1 | 88.6 | 41.8 | 78.9 |
| | | 1 | 5.3 | 94.7 | 82.2 | 17.8 | 89.5 | 41.9 | 78.8 |
| 18.34 | 0.54 | 6 | 6.3 | 93.7 | 82.1 | 17.9 | 87.3 | 42.4 | 79.2 |

Recrystallization of the CPTA CAF D Base salt from 2-propanol increased the optical purity from approximately 87% ee to 98% ee with 87% mass recovery, or 93% recovery based on the (−)-CPTA content of the feed (Table 4).

TABLE 4

Recrystallization of (−)-CPTA CAF D Base from 2-Propanol.

| % ee Feed | wt % Salt Isolated | % ee | M.L. % (+) | M.L. % (−) | wt % Yield | % Yield (−)-CPTA |
|---|---|---|---|---|---|---|
| 86.6 | 13.0 | 97.7 | 48.8 | 51.2 | 87.8 | 93.3 |
| 87.3 | 12.9 | 98.0 | 45.0 | 55.0 | 87.8 | 92.8 |

Overall, an approximately 35% yield out of a maximum 50% of the (−)-CPTA CAF D Base salt, with an optical purity of approximately 98% ee, was obtained from racemic CPTA.

Crystallization of optically enriched enantiomers often increases the chiral purity. Following removal of the resolving agent, crystallization of (−)-CPTA from methylcyclohexanone will also increase the optical purity to some degree. In one experiment, crystallization of (+)-CPTA increased the optical purity from 99.1 to 100% ee; the mother liquor was 95% ee.

Example 3

This example illustrates the solubility profiles of CAF D Base salt of (+)- and (−)-isomers of CPTA in 2-propanol.

To aid in optimization of the CPTA resolution using CAF D Base, the solubility profiles of both of the diastereomeric salts in 2-propanol were determined. The results are shown in FIG. 1. The (+)-CPTA CAF D Base salt was prepared describing the solubilities included in the figure were calculated by least squares analysis ($R^2 > 0.99$). The data point for the (−)-CPTA salt at 82° C. was not included in determining the equation, but closely fits the calculated solubility.

Racemization of the undesired CPTA enantiomer could be recycled back into the process. Thus, it was found that heating an enantiomerically enriched undesired isomer of CPTA in 1 N aqueous sodium hydroxide at reflux resulted in racemization in less than one hour. No other by-products were detected by HPLC analysis of the isolated CPTA.

Example 4

This example illustrates a method for obtaining (+)-CPTA.

A 2-L round-bottom flask with an overhead stirrer was charged with 33.0 g of crude (+)-CPTA—chinconidine salt, 610 mL of ethanol, and 125 mL of methanol. The slurry was heated to reflux to give a solution, then cooled. A very thick slurry formed at 42° C. The slurry was heated to 68° C. to give a light slurry, then allowed to cool to ambient temperature. The mixture was filtered at 26° C. and rinsed with 150 mL of ethanol to give, after drying under vacuum at 40° C., 23.48 g of (+)-CPTA—chinconidine salt. The recrystallization procedure was repeated with 600 mL of ethanol and 120 mL methanol to give 18.23 g of (+)-CPTA—chinconidine salt (55% recovery from two crystallizations). No (−)-CPTA was detected by chiral chromatography, although the degree of separation did not allow for an assessment of low levels (the halofenate chiral analysis conditions were also used at that time for the CPTA analysis).

A 3.61 g sample of the purified salt was mixed with 50 mL of water and 50 mL of toluene, and 2.9 g of sulfuric acid was added. The organic phase was washed with 30 mL of water, then evaporated to a residue. The residue was crystallized from 20 mL of cyclohexane to give 1.22 g of (+)-CPTA. Alternatively, 6.3 g of the (+)-CPTA—chinconidine salt (10.2 mmol) was mixed with 56 g of diethyl ether and 29 g of water, and acidified to a pH of 1.9 with drops of sulfuric acid. The organic phase was washed with 25 mL of water, dried (magnesium sulfate), filtered, and evaporated to a residue. The residue was stirred with 22 mL of methylcyclohexane at ambient temperature to form a slurry. The slurry was warmed to 40° C., then cooled in an ice bath and the solid isolated by filtration to give, after drying at 40° C. under vacuum, 2.62 g (7.92 mmol, 78% yield) of (+)-CPTA.

Example 5

This example illustrates a method for synthesizing (+)-halofenate from (+)-CPTA.

A 25-mL round-bottom flask was charged with 0.91 g of (+)-CPTA and 2.6 g of thionyl chloride, and the mixture heated to reflux to give a solution. Conversion to acid chloride was monitored by quenching a sample with methanol and analyzing the product with HPLC. To the acid chloride solution was added 4.8 g of diethyl ether, and this solution was added to 2.0 g of N-acetylethanolamine in 12 mL of N,N-dimethylformamide (DMF) with 0.37 g of pyridine chilled in an ice bath. The resulting solution was added to 25 mL of water and 30 mL of diethyl ether. The organic phase was separated, washed with 25 ml of water, dried (MgSO₄), and filtered to give, after removal of the solvent, 0.92 g of an oil. HPLC analysis showed 45 area % of halofenate and 50 area % of CPTA. Chiral HPLC analysis indicated that the halofenate was 99.78% ee of the (+)-enantiomer.

Example 6

This example illustrates a method for preparing racemic CPTA.

A 2-L round-bottom flask with an overhead stirrer was charged with 102.7 g of halofenate, 500 mL of water, and 16.3 g of 2-propanol. The slurry was stirred, and 32.3 g of aqueous 45% potassium hydroxide was added. After heating to reflux for 1 hour, the solution was cooled to ambient temperature and charged with 380 mL of hexanes. The pH was adjusted from 12.5 to 2 with 24.57 g of 37% hydrochloric acid. The three phase mixture was heated to 60° C. to give two phases. The lower aqueous phase was removed and extracted with 50 mL of hexanes. The combined organic layers were heated to distill at atmospheric pressure to remove 100 mL of cloudy distillate. The solution was cooled to 30° C. and seeded with CPTA. A slurry formed. The slurry was cooled in an ice bath and the solid isolated by filtration to afford 64.0 g (78.4% yield) of racemic CPTA, i.e., (4-chlorophenyl)(3-trifluoro-methylphenoxy)acetic acid.

Example 7

This example shows representative results of chiral resolution screening in ethanol using a variety of chiral bases.

A sample of 1.16 g (3.51 mmol) of CPTA was dissolved in 6.98 g of ethanol to give a solution (0.431 mmol/g). Glass vials were individually charged with the amounts of each base listed in Table 5, and the amount of the ethanolic CPTA solution calculated to give a 1 to 1 molar ratio of acid to base was added. In some cases, a small amount of ethanol was added to wet the base prior to addition of the CPTA solution. The vials were allowed to stand overnight at ambient temperature. Vials 7G and 7I gave precipitates. A sample of each supernate was removed and analyzed by chiral HPLC analysis. The solids were isolated by filtration, and also analyzed. Some of the results are shown in Table 2 (see Example 1 above). The remaining vials were placed in a refrigerator at 5° C. After one day, 7E give a precipitate. The sample was analyzed as previously described. The remaining vials were charged with 50 μL of water, and held at ambient temperature for three days before placing in the refrigerator. No additional precipitates were noted after one month.

TABLE 5

Base Screening in Ethanol.

| | Base | wt CPTA Solution (g) | Wt Base (g) | EtOH Added | Water Added |
|---|---|---|---|---|---|
| 7A | S-(−)-Methylbenzylamine | 0.8836 | 0.4620 | 0 g | 0.05 g |
| 7B | 1-2-Amino-1-butanol | 0.8198 | 0.0314 | 0 | 0.05 |
| 7C | (1R,2S)-(−)-Norephedrine | 0.5273 | 0.0342 | 0.2007 | 0.05 |
| 7D | (1S,2S)-(+)-Pseudoephedrine | 0.7295 | 0.0515 | 0.1459 | 0.05 |
| 7E | (1S,2S)-(+)-2-Amino-1-(4-nitrophenyl)-1,3-propanediol | 0.5580 | 0.0510 | 0.1228 | 0 |
| 7F | (1,2S)-(+)-2-Amino-1-phenyl-1,3-propanediol | 0.5640 | 0.0405 | 0.1287 | 0.05 |
| 7G | (−)-Cinchonidine | 0.3484 | 0.4390 | 0.3637 | 0 |
| 7H | (+)-Cinchonine | 0.6409 | 0.0796 | 0.2103 | 0.05 |
| 7I | Quinine | 0.5391 | 0.0750 | 0.1735 | 0 |
| 7J | (−)-Strychnine | 0.5812 | 0.0828 | 0.2295 | 0.05 |
| 7K | Brucine | 0.7566 | 0.1287 | 0 | 0.05 |
| 7L | (S)-(+)-2-pyrrolidine-methanol | 0.8681 | 0.0383 | 0 | 0.05 |

Example 8

This example shows representative results of chiral resolution screening in acetone using a variety of chiral bases.

A sample of 1.67 g of CPTA was dissolved in 7.57 g of HPLC grade acetone to give a solution. Glass vials were individually charged with the amounts of each base listed in Table 6, and the amount of the CPTA solution calculated to give a 1 to 1 molar ratio of acid to base was added. In some cases, a small amount of acetone was added and the mixture was warmed to about 40° C. to give a solution. Additionally, 0.300 mL of 1 N sodium hydroxide was added to vial 16M. The vials were allowed to stand overnight at ambient temperature. Vial 16D formed a precipitate, and was analyzed as described above. Some of the results are summarized in Table 2 (see Example 1). The remaining vials were placed in the refrigerator. Vial 16 N formed a precipitate, and was analyzed. Vial 16G formed a very light precipitate. After one week, vial 16L was found to contain a precipitate. The sample was analyzed as previously indicated. No additional precipitates were noted.

TABLE 6

Base Screening in Acetone.

| | Base | wt CPTA Solution (g) | Wt Base (g) | Acetone Added (g) |
|---|---|---|---|---|
| 16A | (1R,2S)-(−)-Norephedrine | 0.8568 | 0.0704 | |
| 16B | (1S,2S)-(+)-2-Amino-1-phenyl-1,3-propanediol | 0.1824 | 0.0168 | |
| 16C | S-(−)-Methylbenzylamine | 0.8948 | 0.0592 | |
| 16D | Quinine | 0.1968 | 0.0347 | 0.85 |
| 16E | (S)-(+)-2-pyrrolidine-methanol | 0.8181 | 0.0452 | |
| 16F | Brucine | 0.2163 | 0.0463 | |
| 16G | (+)-Cinchonine | 0.3987 | 0.0630 | |
| 16H | (1S,2S)-(+)-Pseudoephedrine | 1.0835 | 0.0974 | |
| 16I | (−)-Strychnine | 0.1462 | 0.0265 | 0.25 |
| 16J | Quinidine | 0.3753 | 0.0663 | |
| 16K | 1-2-Amino-1-butanol | 0.7248 | 0.0353 | |
| 16L | L-Tyrosine Hydrazide | 0.4508 | 0.0472 | 0.39 |
| 16M | L-Leucine Methyl Ester Hydrochloride | 0.5585 | 0.0544 | |
| 16N | Quinine | 0.4712 | 0.0829 | 2.00 |
| 16O | (+)-Cinchonine | 0.3363 | 0.0539 | 0.30 |

Example 9

This example shows representative results of chiral resolution screening in methanol using a variety of chiral bases.

A sample of 2.00 g of CPTA was dissolved in 8.03 g of HPLC grade methanol to give a solution. Glass vials were individually charged with the amounts of each base listed in Table 7, and the amount of the CPTA solution calculated to give a 1 to 1 molar ratio of acid to base was added. Additionally, 0.300 mL of 1 N sodium hydroxide was added to vial 27J. The vials were allowed to stand overnight at ambient temperature. Vial 27B solidified, and an additional 300 μL of methanol was added before the sample was analyzed as described above. The remaining vials were placed in the refrigerator. No additional precipitates were noted after one month.

TABLE 7

Base Screening in Methanol.

| | Base | wt CPTA solution (g) | wt base (g) |
|---|---|---|---|
| 27A | (1R,2S)-(−)-Ephedrine | 0.4896 g | 0.0478 g |
| 27B | Quinine | 0.1420 | 0.0282 |
| 27C | (+)-Cinchonine | 0.1822 | 0.0324 |
| 27D | 1-2-Amino-1-butanol | 1.0012 | 0.0539 |
| 27E | S-(−)-Methylbenzylamine | 0.7892 | 0.0576 |
| 27F | (1S,2S)-(+)-Pseudoephedrine | 0.7600 | 0.0749 |
| 27G | Brucine | 0.1891 | 0.0436 |
| 27H | Quinidine | 0.5845 | 0.1144 |
| 27I | (1S,2S)-(+)-2-Amino-1-phenyl-1,3-propandiol | 0.3032 | 0.0299 |
| 27J | L-Leucine Methyl Ester Hydrochloride | 0.5033 | 0.0545 |
| 27K | (S)-(+)-2-Pyrrolidine-methanol | 0.7133 | 0.0434 |
| 27L | (1R,2S)-(−)-Norephedrine | 1.1788 | 0.1070 |
| 27M | (−)-Strychnine | 0.4525 | 0.0905 |
| 27N | (S)-(+)-2-Amino-3-methyl-1-butanol | 0.1478 | 0.0092 |
| 27O | (S)-(+)-2-Amino-1-propanol | 0.9268 | 0.0417 |
| 27P | (S)-(−)-2-mino-3-phenyl-1-propanol | 0.3406 | 0.0307 |

Example 10

This example shows the result of resolving CPTA with quinine.

A 150-mL jacketed bottom-drain flask was charged with 2.70 g (8.17 mmol) of CPTA, 2.65 g (8.17 mmol) of quinine, and 50 mL of 2-propanol. The mixture was heated to 70° C. to give a solution, then cooled to 30° C. at a rate of 0.2° C./min and held for 2 hours to give a slurry. Chiral HPLC analysis of a sample showed 42.88 and 56.47 area % of (+) and (−)-CPTA, respectively, in the solid phase, and 61.54 and 34.19 area % of (+) and (−)-CPTA, respectively, in the solution. The slurry was heated to 60° C., then cooled to 30° C. at a rate of 0.04° C./min and held overnight to give a slurry. Chiral HPLC analysis showed 29.94 and 44.19 area % of (+) and (−)-CPTA, respectively, in the solid phase, and 77.54 and 20.88 area % of (+) and (−)-CPTA, respectively, in the solution. The slurry was diluted with 50 mL of 2-propanol and heated to 57° C. to give a solution, then cooled to 30° C. at a rate of 0.2° C./min. A slurry started to form after 1 hour at 30° C. The mixture was stirred for 2 days at ambient temperature, then the solid was isolated by filtration and rinsed with 2-propanol to give, after drying under vacuum, 2.89 g (54% yield by mass) of the quinine salt of CPTA. Chiral HPLC analysis found 42.25 and 57.75 area % of (+) and (−)-CPTA, respectively, in the solid phase and 56.56 and 39.20 area % of (+) and (−)-CPTA, respectively, in the mother liquor. The results are also included in Table 2 (see Example 1).

Example 11

This example shows the result of resolving CPTA with CAF D base.

A 150-mL bottom-drain flask was charged with 19.54 g of CPTA, 6.82 g of CAF D Base (i.e., D-threo-(−)-2-amino-1-(nitrophenyl)-1,3-propandiol), and 80.2 g of 2-propanol. The mixture was warmed to 70° C. to give a solution, then cooled to a jacket temperature of 5° C. at a rate of 0.1° C./min. The mixture was hazy at 62° C. After holding at 6° C. for 9 hours, the solid was isolated by filtration, rinsed with 5 mL of 2-propanol, and dried at 40° C. under vacuum to give 12.03 g (37.4 wt % yield) of (−)-CPTA CAF D Base salt. Chiral HPLC analysis of the solid found 6.34 area % of (+)-CPTA and 93.46 area % of (−)-CPTA; the mother liquor contained 81.41 area % of (+)-CPTA and 17.76 area % of (−)-CPTA.

Example 12

This example shows the result of recrystallizing (−)-CPTA CAF D Base salt.

A 150-mL bottom-drain flask was charged with 8.00 g of the (−)-CPTA CAF D Base salt (from Example 11 above) and 54.2 g of 2-propanol. The mixture was heated to reflux to give a solution, then cool to a jacket temperature of 20° C. at a rate of 0.1° C./min and held at an internal temperature of 22° C. for 6 hours. The solid was isolated by filtration, rinsed with 2-propanol, and dried at 40° C. under vacuum to give 6.93 g (86.6 wt % recovery) of (−)-CPTA CAF D Base salt (m.p. 184-185° C.). The solid contained 0.995 area % of (+)-CPTA and 99.01 area % of (−)-CPTA; the mother liquor contained 44.53 area % of (+)-CPTA and 54.47 area % of (−)-CPTA. The reactor was cleaned out with acetone. The acetone was evaporated to a residue of 0.27 g (3.4 wt %).

Example 13

This example illustrates a method for preparing (+)-CPTA CAF D Base salt.

A 1-L flask was charged with 10.94 g (17.5 mmol) of the (+)-CPTA cinchonidine salt, 200 mL of water, and 100 mL of methylene chloride. The pH was adjusted to 1.9 by the addition of 1.8 g of sulfuric acid. The organic layer was washed three times with 100-mL portions of dilute aqueous sulfuric acid, dried (magnesium sulfate), filtered, and evaporated to a residue of 5.79 g. The residue was dissolved in 22.2 g of 2-propanol, and 3.5 g of CAF D Base was added. The resulting slurry was heated to reflux to give a solution, then cooled to ambient temperature and the slurry stirred for three hours. After cooling in an ice bath, the solid was isolated by vacuum filtration, rinsed with 5 mL of 2-propanol, and dried under vacuum at 40° C. to give 7.39 g (80% yield) of (+)-CPTA CAF D Base salt (m.p. 172-173° C.).

Example 14

This example shows solubility of diastereomeric CPTA-CAF D base salts in 2-propanol.

Samples of (−)-CPTA CAF D Base and (+)-CPTA CAF D Base (>98% ee) were added to 2-propanol in the amounts shown in Table 8, and mixed using an ultrasonic bath. All samples remained slurries. The slurries were held overnight at the temperature listed, then samples of the supernates were removed and analyzed by quantitative HPLC analysis to determine the CPTA concentration. The results are shown in the table, and in FIG. 1. Additionally, 8.00 g of (−)-CPTA CAF D Base salt required 54.2 g of 2-propanol for solution at 82° C. (14.7 wt %). This data point was included in FIG. 1, but not included in the solubility equation.

TABLE 8

Solubility in 2-Propanol.

| Wt Salt (g) | Wt 2-propanol (g) | T ° C. | Wt % in solution |
|---|---|---|---|
| (−)-CPTA CAF D Base Salt | | | |
| 0.31 | 1.17 | 45.3 | 2.35 |
| 0.23 | 2.48 | 7.8 | 0.376 |
| 0.21 | 1.31 | 19.4 | 0.688 |
| (+)-CPTA CAF D Base Salt | | | |
| 0.25 | 1.84 | 20.0 | 1.85 |
| 0.27 | 1.83 | 45.8 | 6.03 |
| 0.17 | 2.09 | 8.5 | 1.32 |

Example 15

This example illustrates a method for racemizing enantiomerically enriched CPTA.

A 50-mL round bottom flask was charged with 0.31 g of (−)-CPTA (68.7% ee) and 9.4 g of 1 N sodium hydroxide. The solution was heated to reflux for one hour, then cool to ambient temperature and acidified with 1 g of 37% hydrochloric acid. The CPTA was extracted into methylene chloride, and the solvent was evaporated to an oil of 0.46 g. HPLC analysis found 99.4 area % of CPTA, and chiral HPLC analysis found a 50/50 mixture of the CPTA enantiomers.

Example 16

This example illustrates a process for resolving a racemic mixture of CPTA using CAF D-Base under a variety of crystallization conditions.

The general crystallization procedure was to charge CPTA, CAF D-Base, and 2-propanol at room temperature and heat to a solution at about 75° C. The solution was cooled to about 60° C. and held until nucleation occurred. Several batches were seeded with (−)-Salt (i.e., salt of (−)-CPTA and CAF D-Base) to induce nucleation. After the slurry had developed over about an hour, the vessel was cooled to the isolation temperature. The first 5 entries in FIG. 2 used a slow cooling rate of about 0.05–0.10° C./minute to reach the isolation temperature. The other experiments used a faster cooling rate of 0.25–0.40° C./minute. A fiber optic probe is inserted directly into the crystallizer to determine the slurry density.

The amount of CAF D-Base added and the solute concentration are some of the important variables which give rise to the final batch composition. The tendency for the (+)-Salt (i.e., salt of (+)-CPTA and CAF D-Base) to remain supersaturated for varying amounts of time is believed to be a major cause for variability in some experiments. This is demonstrated in entry 5 in FIG. 2, whereby the slurry was held for 8 hours at 13° C. and produced high purity crystal (99.7% (−)-Salt). Three hours later, an increase in the signal of the fiber optic probe indicated the likely nucleation of the (+)-Salt. After another 27 hours, the slurry was isolated and the crystal product contained a (−/+)-CPTA ratio of 83.3/16.7%. Analysis of the crystal product by HPLC gives the ratio of (−)-CPTA and (+)-CPTA. Since the free CPTA in solution is undersaturated the crystal analysis therefore gives the diasteriomeric salt ratio. Mother liquors contain both dissolved salt and free CPTA. Analysis by HPLC reports the combined amount of each enantiomer as CPTA. Similarly, entry 6 of FIG. 2 shows that the slurry was held for 20 hours at 1° C. and produced high purity salt (>98% (−)-CPTA). After heating to 17° C., the (+)-Salt nucleated and gave poorer quality product [(−/+)-CPTA=81.2/18.8%].

In other trials, nucleation of the (+)-Salt occurred more quickly, as in entries 2, 8, and 10 of FIG. 2. A crystallization is desirable for which isolation could be done near, preferably just above, the saturation temperature of the (+)-Salt.

At a loading of 3.9 g of 2-propanol per gram of CPTA and with 0.45 equivalent of CAF D-Base, an isolation at room temperature appears to be very near the saturation level (or within the metastable zone) of the (+)-Salt. Entry 12 in FIG. 2 started with 0.43 equivalents of base, and the crystal product at 21° C. remained pure (>99% (−)-Salt), even after seeding with (+)-Salt. After adding more CAF D-Base to give 0.45 equivalents, the slurry was held for 14 hours, and then for 6 more hours after seeding with (+)-Salt. The crystal product analyzed at 98.7% (−)-CPTA ratio. Increasing the total base to 0.47 equivalent gave crystal product which slowly increased in (+)-Salt composition to (−/+)-CPTA=92.3/7.7%.

Entry 11 of FIG. 2 (3.9 g of 2-propanol per gram of CPTA, 0.45 eq. base) maintained high purity of the (−)-Salt (99.1%) after 14 hours, but upon addition of more base to 0.48 eq., the resulting ratio of the product was (−/+)-Salt=89.2/10.8%. Entry 9 of FIG. 2 (at 0.45 eq. base) maintained 99.5% (−)-Salt purity after 16 hours at 22° C. Calculated yields of (−)-CPTA from the three batches under these conditions were 70.7–71.6%. Calculated yields are derived from a forced mass balance from the racemic CPTA feed, by knowing the crystal and mother liquor composition of (−)-CPTA and (+)-CPTA.

These loadings of about 0.45 equivalent of CAF D-Base and about 4 g of 2-propanol per gram of CPTA provide a high purity (−)-Salt (>98.5%) product, which can be used without a further recrystallization.

Example 17

This example provides a model to describe the resolution/crystallization of CPTA salt.

Figure 3:
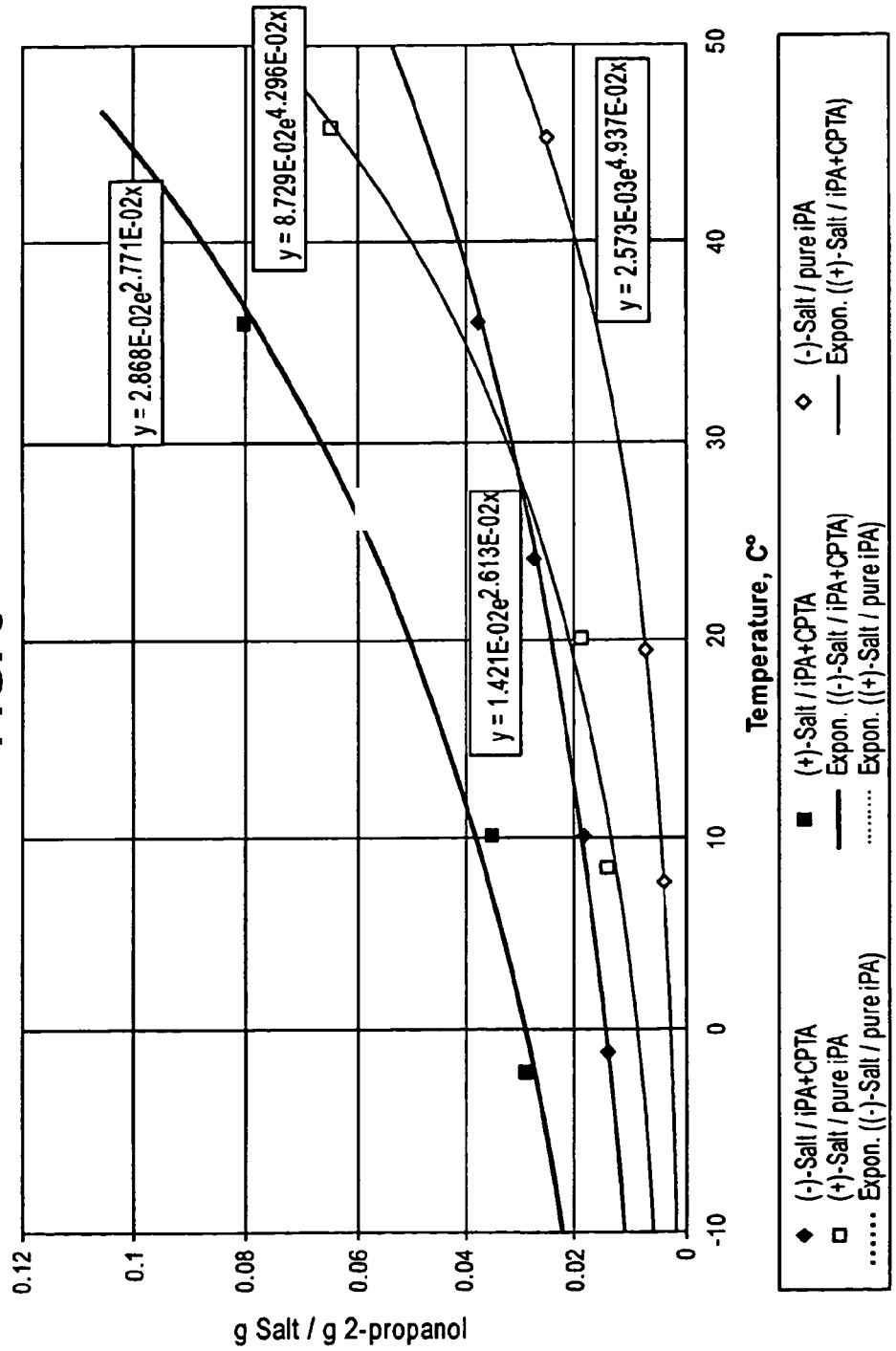
FIG. 3 is a graph showing the solubility of (−)- and (+)-CPTA/CAF D-Base salts in pure isopropanol and a solution comprising a mixture of isopropanol and CPTA (11%).

The concentration of free CPTA depends on the amount of base charged and the solvent loading. For example, a resolution of CPTA by charging 4.0 grams of 2-propanol and 0.50 equivalent of CAF D-Base, results in formation of the salt in 2-propanol which contains 11% free CPTA. This solvent possesses greater solubility for both the (−)-Salt and the (+)-Salt, and was determined as shown in FIG. 3. FIG. 3 also includes the solubility data in pure 2-propanol, expressed in gram of component per gram of 2-propanol. As FIG. 3 shows the curves for the respective salts are of similar shape.

Figure 4:
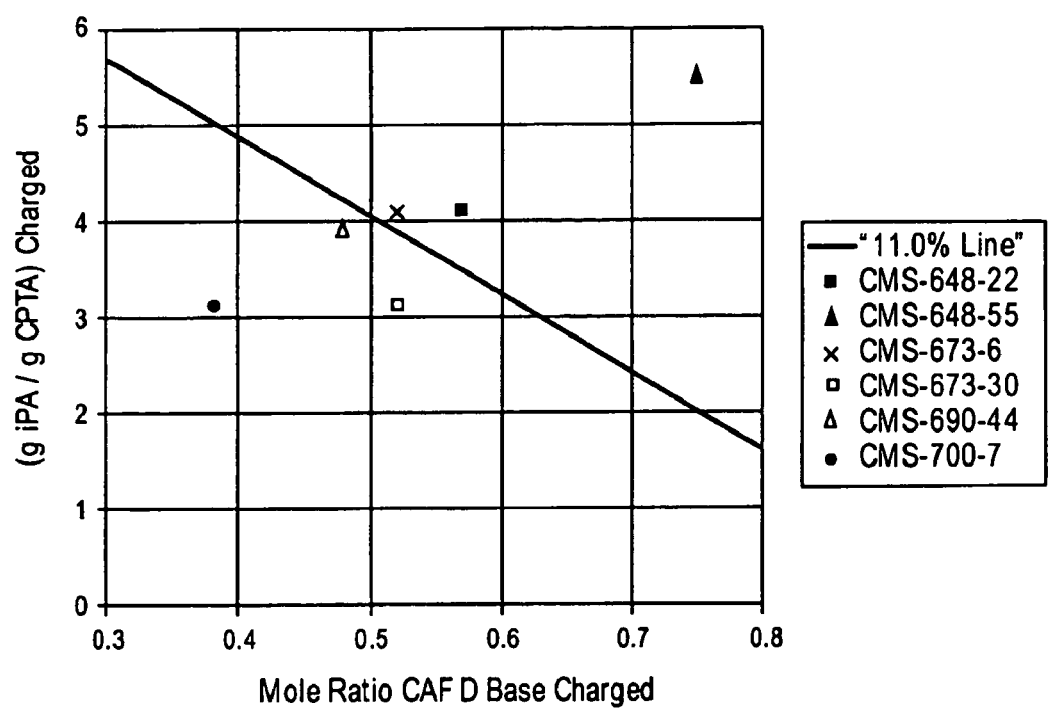
FIG. 4 is a graph showing the composition of a mixture with a various amount of each components.

By other combinations of the loading of CPTA, CAF D-Base, and 2-propanol, a system resulting in 11.0% free CPTA in 2-propanol can also be attained, as shown in FIG. 4. As FIG. 4 shows, the loading for various experiments in FIG. 2 did not usually fall exactly on this line. However, the (−)-Salt and the (+)-Salt solubility can be estimated as follows: a loading which gives a point above the "11.0% free CPTA" line is more dilute (i.e., <11.0% free CPTA in 2-propanol), and exhibits a lower solubility than the "11.0%" line. Conversely, points below the "11.0%" line result in solvent containing >11.0% free CPTA, and the salt solubility is greater than determined in FIG. 3. To estimate component solubility, a constant multiplier factor, k, was used. The modified solubility equations for the (−)-Salt and the (+)-Salt are therefore $S_{(-)}=0.01421ke^{0.02613T}$ and $S_{(+)}=0.02868ke^{0.02771T}$.

Figure 5:
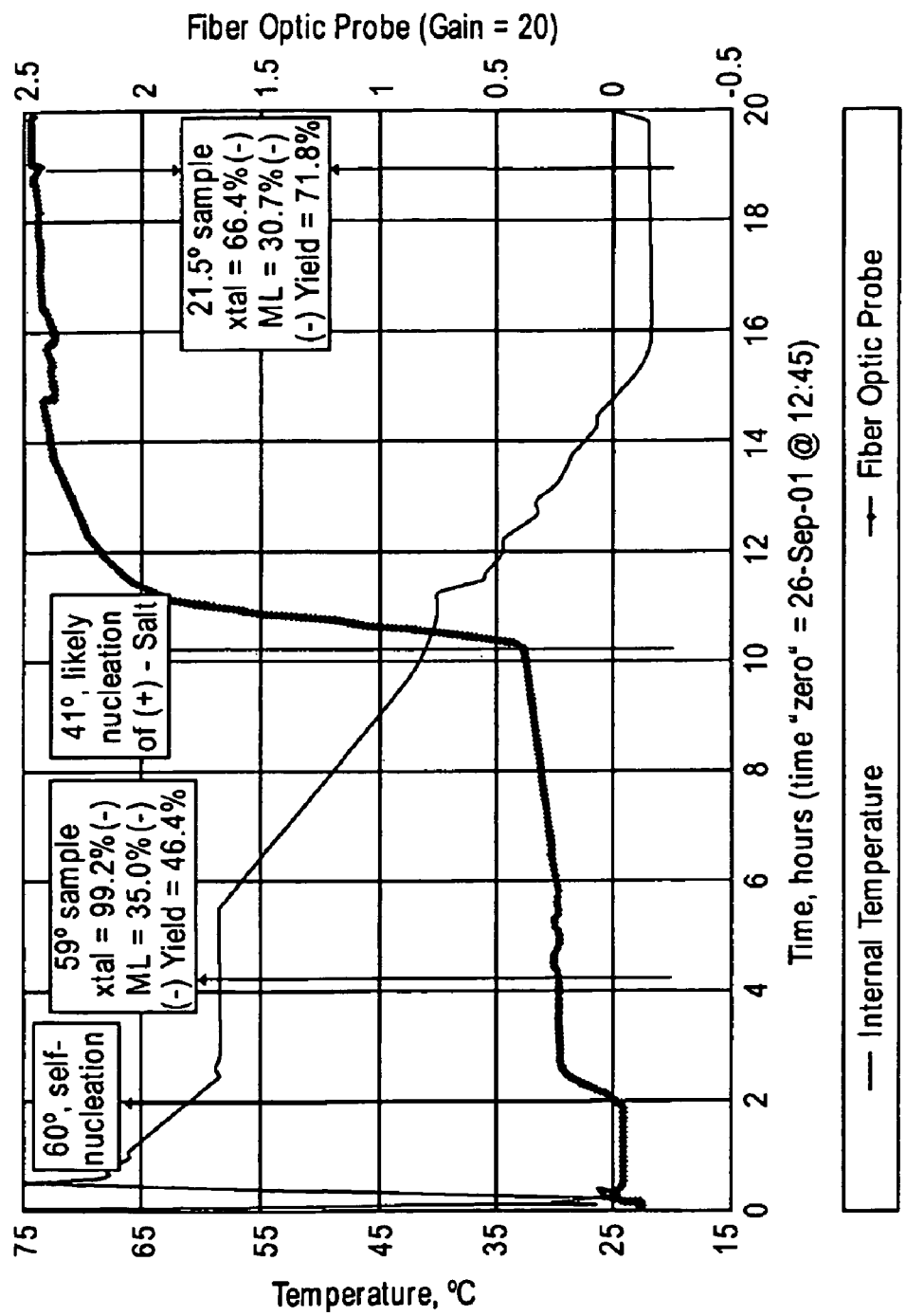
FIG. 5 is a graph showing a (−/+)-salt saturation profile for crystallization and heating.
Figure 5:
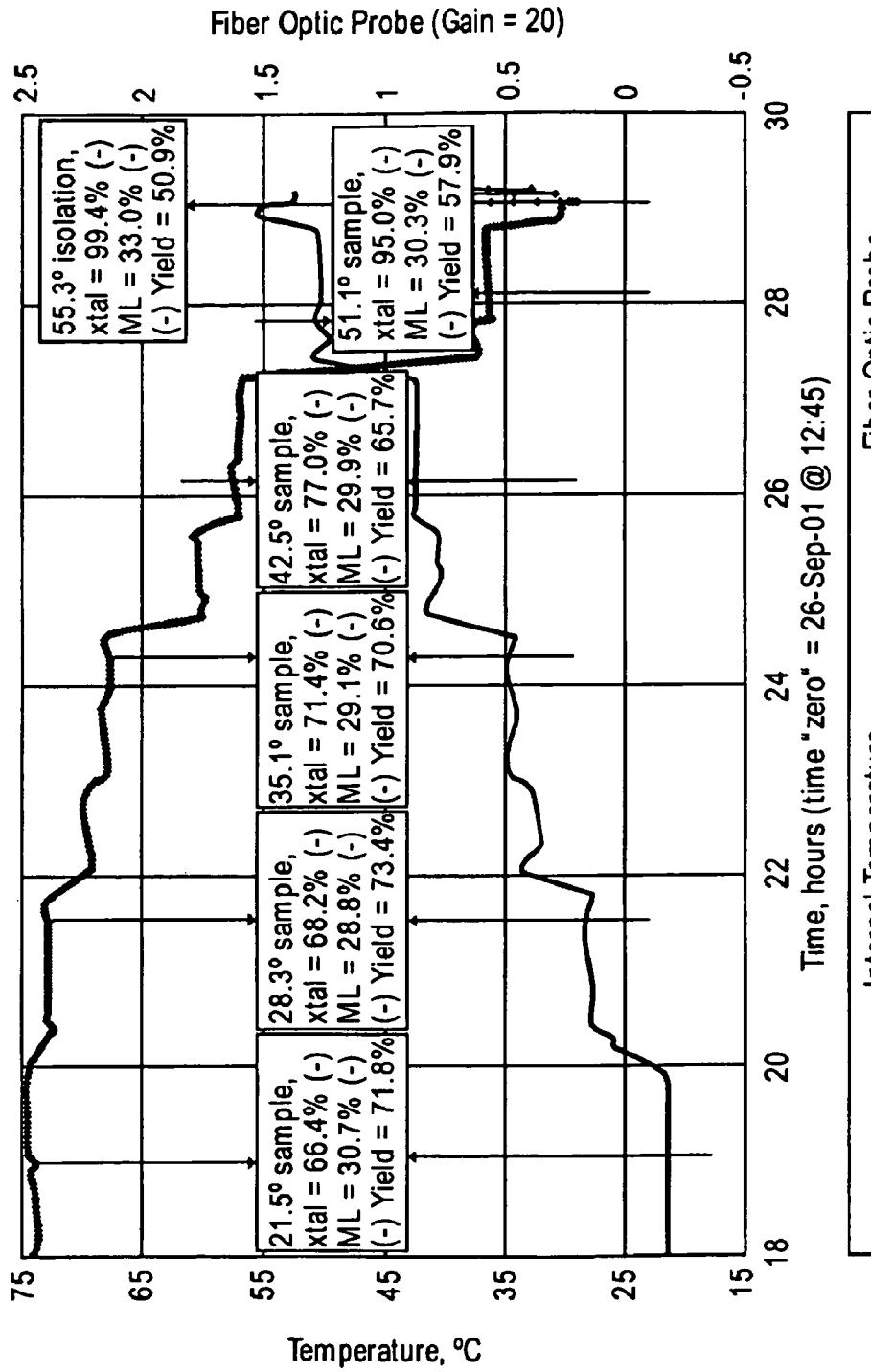

Even with a good estimation of the (−)-Salt and the (+)-Salt solubility by adjusting k, one can still not describe the crystallization, for the other unknown is the ratio of (−)-Salt and (+)-Salt which is formed upon addition of the resolving agent base. One of the more detailed experiments is shown in FIG. 5 (see also FIG. 2). This experiment used 0.75 equivalent of base and when sampled at 21.5° C., gave the product with (−/+)-Salt ratio of 66.4/33.6%. By heating the slurry and continuing to take samples, the saturation line for both (−)-Salt and the (+)-Salt in the solvent can be followed.

To match the solubility model to the actual data, a regression technique was used, whereby the solubility factor k and the feed ratio of (−)-Salt and (+)-Salt were manipulated to give an answer (i.e., crystal composition, mother liquor composition, and crystal yield) which was consistent with the observed data. By selecting k=0.68 and a feed ratio for 0.75 equivalent of salt at 58.1% (−)-Salt/41.9% (+)-Salt (i.e., 0.436 eq. of (−)-Salt and 0.314 eq. of (+)-Salt were formed upon addition of CAF D-Base), a good agreement was obtained. FIG. 6 shows the comparison. The solubility model allows calculation of the complete mass balance for the isolation: the amount of (−)-Salt and (+)-Salt in the crystal, the amount of (−)-Salt and (+)-Salt in the mother liquor, and also the amount of (−)-free CPTA and (+)-free CPTA in the mother liquor. One procedure for quantifying (−/+)-Salt and (−/+)-free CPTA in mother liquor by an extractive work-up, using solubility differences, is provide in Example 19 below.

Figure 7:
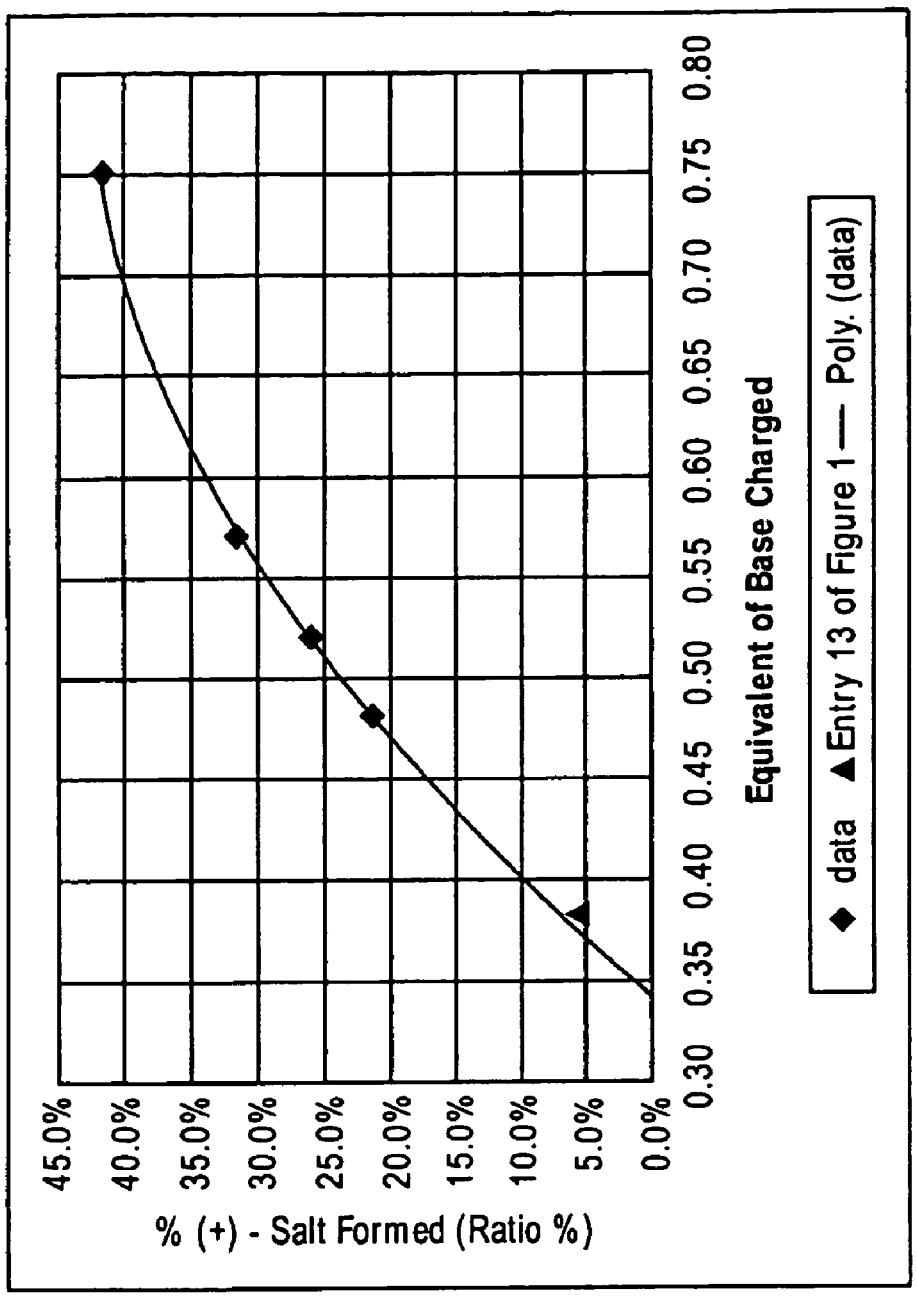
FIG. 7 is a graph showing the amount of (+)-salt formation as a function of the amount of CAF D-Base added.

The regression technique with the solubility model was applied to other experiments which fed differing amounts of resolving agent. Using a combination of the solubility factor k and the composition of the salt as feed (i.e., the ratio of (−)-Salt and (+)-Salt which was formed upon the addition of base), the model tended to a unique solution which fit the experimental results. From these, the graph in FIG. 7 was constructed. This result shows that as more resolving agent is added (above the extrapolated minimum point of 0.34 eq.), an increasing amount of (+)-Salt is formed. Without being bound by any theory, in some embodiments, it is believed that if less than 0.34 equivalent is added, the CAF D-Base will coordinate substantially only with (−)-CPTA, forming almost exclusively (−)-Salt. Additionally, by aid of the curve in FIG. 7, the amount of (−)-CPTA and (+)-CPTA (free acid) can be calculated. Between 0.35–0.75 equivalent of base charged, the % ratio of {(−)-CPTA/total CPTA free acid} is around 25% (23.3–27.1%). The "selectivity" for the ratio of (−/+)-Salt that is formed thus is dependent on the amount of free (−)-CPTA that remains (in solution), which comes to an endpoint of about (−)-CPTA/(+)-CPTA =1/3. It is believed that once the (−)-CPTA concentration is depleted by addition of about 0.34 eq. of base to a (−/+)-CPTA ratio of 1/3, continued addition of base forms the (−/+)-Salt at a ratio of 3/1 (to keep free (−/+)-CPTA at a constant 1/3 ratio in solution).

Example 18

This example illustrates resolution of a racemic mixture of CPTA.

Figure 8:
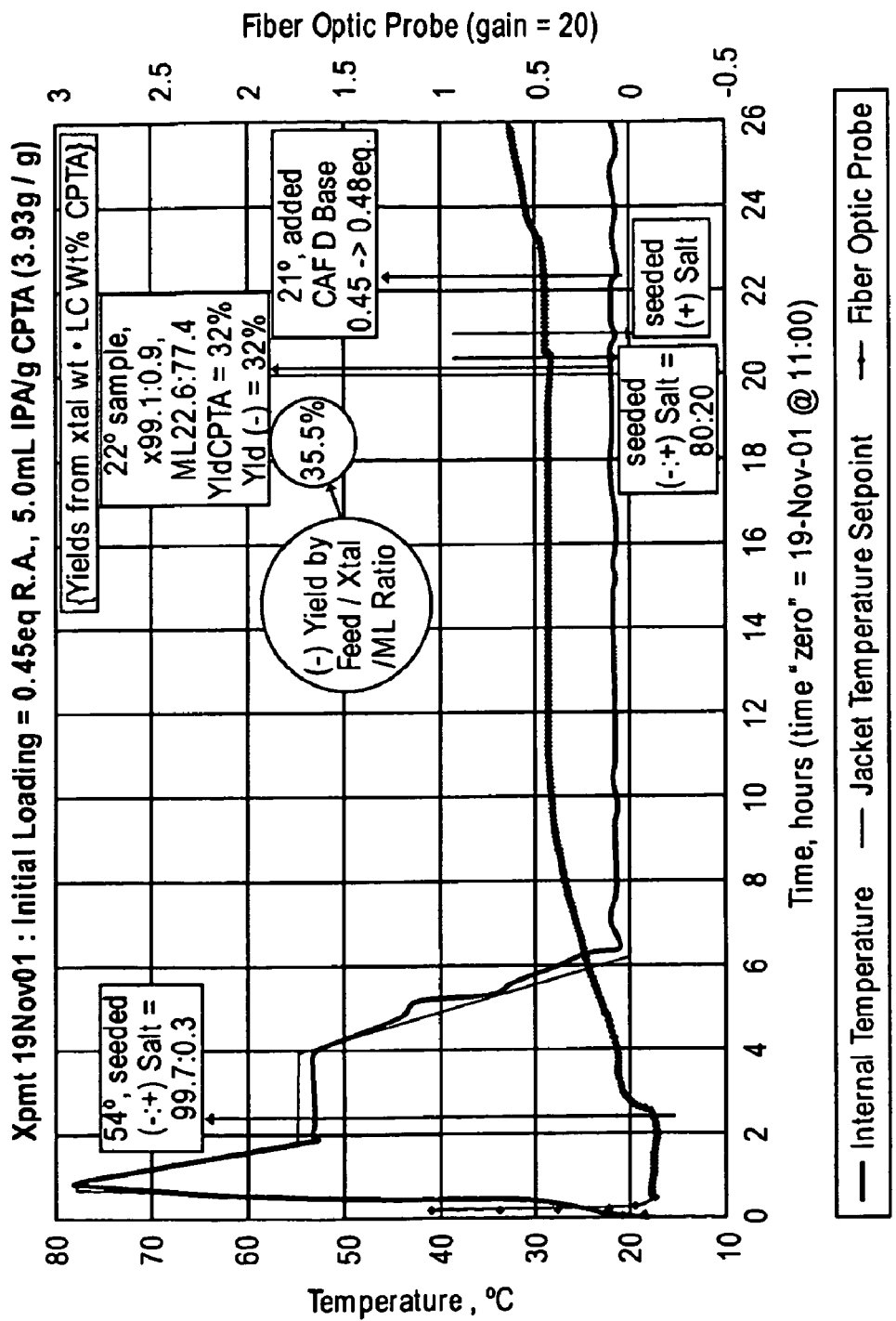
FIG. 8 is a graphic representation of experimental data for the resolution shown in entry 11 of FIG. 2.
Figure 8:
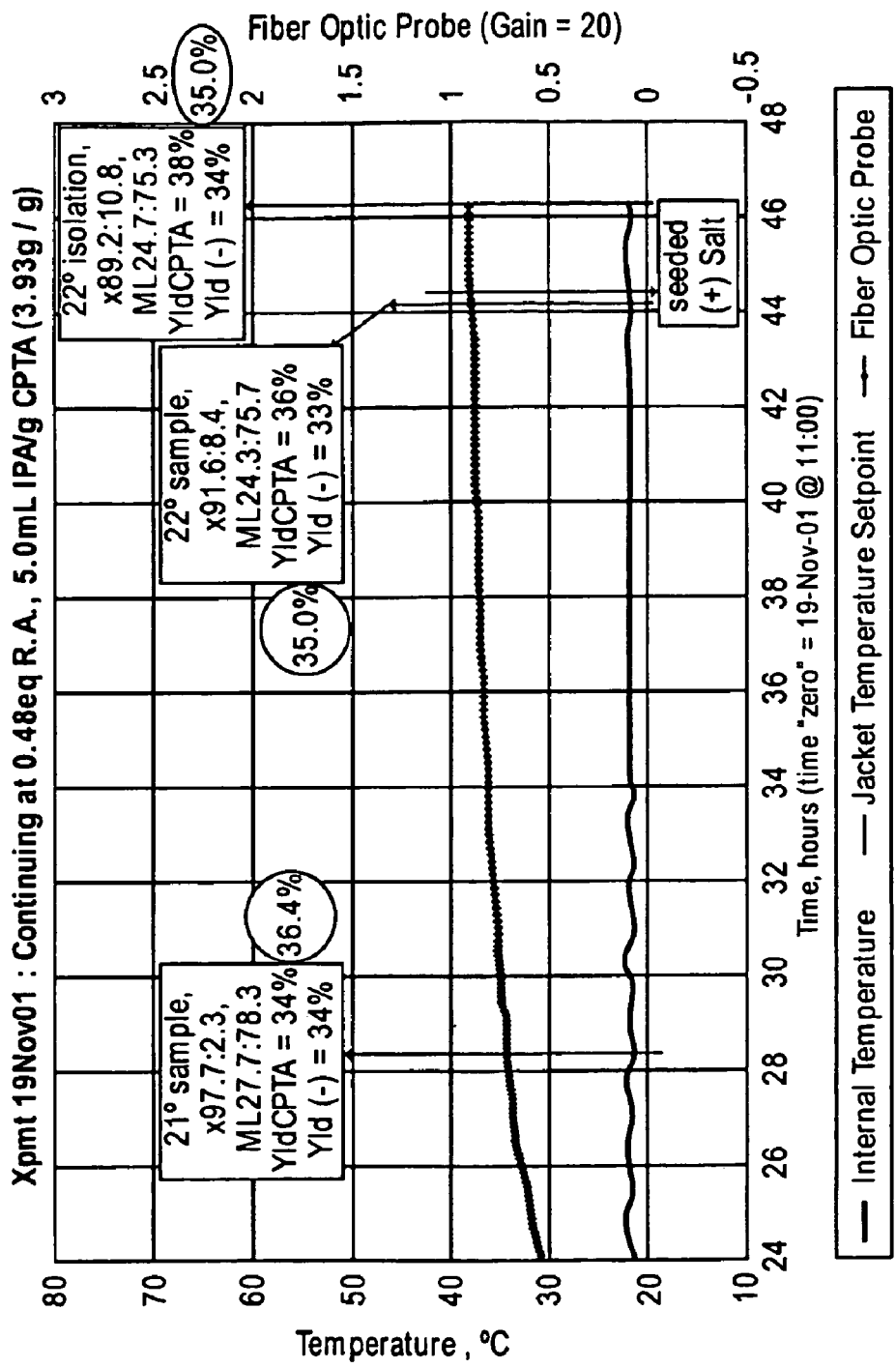

A 200-mL vessel was charged with 17.0 g of CPTA (51.4 mmol), 4.91 g of CAF D-Base (23.1 mmol, 0.450 eq.), and 85 mL of 2-propanol. The mixture was heated to a solution at 78° C., and then cooled at 0.5° C./min to 54° C. About ½ hour later, the solution was seeded with (−)-Salt to induce nucleation. After holding at 54° C. for about 1-½ hours, the slurry was cooled to 22° C. at 0.25° C./minute. After holding for 14 hours at 22° C., a small sample (~5 mL) was taken and separated on a 15-mL, medium-fritted funnel. The mother liquor was weighted and saved, and the solid was washed with 2 mL of 2-propanol. The wash was weighed and saved, and suction was continued to dry the crystal. Analysis by the standardized HPLC system allowed calculation of weight % (−)-CPTA and (+)-CPTA in each stream. A mass balance around this sample (total accountability of CPTA in the crystal, mother liquor, and wash was 0.85 g) gave a 31.9% isolated yield of crystal product from the total CPTA. Crystal purity was 99.1/0.9%=(−/+)-CPTA ratio by weight. FIG. 8 shows the analytical and mass balance results in the rectangular boxes. The calculated yield (from CPTA) based on feed/mother liquor/crystal composition is given inside the circles. Abbreviations in FIG. 8 are as follows: R.A.=resolving agent, x or xtal=crystal, ML=mother liquor, Yld=yield.

The vessel was seeded several times with crystal containing (+)-Salt, and about 2 hours later, 0.31 g of CAF D-Base (1.46 mmol, ~0.03 eq.) was added. The vessel was sampled two times (see FIG. 8) before the final isolation on a 60-mL medium-fritted funnel. The mother liquor was clear, pale yellow-gold, 59.1 g. The solid was washed with 19.2 g of 2-propanol, with recovery of 18.8 g of wash solution. The washed solid (10.07 g) was further dried by suction on the funnel for an hour to 8.36 g (15.4 mmol salt). Analysis of all streams from the final isolation accounted for 13.45 g (40.67 mmol) of CPTA. The final crystal product ratio was (−/+)-CPTA=89.2/10.8%, for an isolated yield of (−)-CPTA=33.8%/a (from CPTA). The calculated yield of (−)-CPTA, based upon the feed, mother liquor, and crystal composition, was 35.0%.

Example 19

This example illustrates an extractive work-up process to quantify (−/+)-Salt and (−/+)-CPTA in Mother Liquor.

Figure 9:
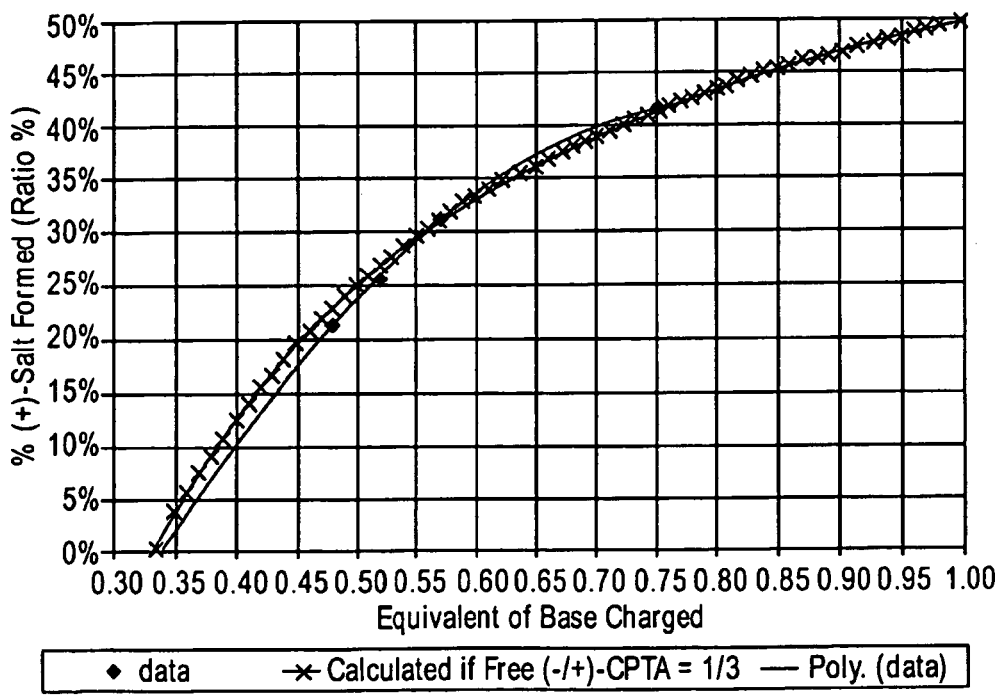
FIG. 9 shows the actual and calculated amount of CPTA in mother liquor and a graphic comparison of a calculated percentage of (+)-CPTA salt with the experimental data.

A mixture of the (−/+)-Salt, 80/20, was only sparingly soluble in methylene chloride at about 0.016%, while racemic CPTA was considerably more soluble at a little less than 3.4%. The final mother liquor from separation of entry 4 of FIG. 2 at 55.3° C. (see FIGS. 2 and 5) was analyzed by evaporating 0.1286 g to a glassy residue of 0.0242 g. The residue was dissolved in 5 mL of methylene chloride, seeded with (−/+)-Salt=80/20, and allowed to stand overnight. The bulk of the supernatant liquid was removed, 3 mL of methylene chloride were added, and the bulk of the liquid was removed and combined with the first extract. The methylene chloride extract was evaporated to give a glassy solid, 0.0074 g, and then analyzed by HPLC. The remaining thick slurry was evaporated to 0.0162 g and analyzed by HPLC. Results from the extractive work-up procedure are generally similar to the composition predicted by the solubility model, as shown in FIG. 9.

Example 20

This example shows solubility of (−)- and (+)-CPTA·CAF D-Base salts in alcohols containing CPTA.

"Solvent" was prepared by dissolving 2.40 g of racemic CPTA in 19.42 g of 2-propanol (Fisher HPLC Grade) or 4.90 g of racemic CPTA in 31.4 g of ethanol. The respective concentrations of CPTA in solution were 11.0% and 13.5%. Solubility of the (−)-CPTA·CAF D-Base Salt (i.e., (−)-Salt) or (+)-CPTA·CAF D-Base Salt (i.e., (+)-Salt) was determined by a gravimetric method. At a given temperature, a portion of the supernatant liquid from a saturated solution was remove to a vial of known weight. The solution weight was determined, and the volatile solvent was evaporated with a purge of nitrogen. The solid was further dried to constant weight in a vacuum oven at about 50° C./1 mm Hg. The vial was re-weighed to determine the loss of volatile solvent and weight of solid remaining. From this, the amount of dissolved CPTA from the "solvent" could be calculated. Subtracting the weight of total solid from the CPTA gave the weight of soluble salt in the solvent. Data are shown in FIGS. 10A and 10B.

Example 21

This example illustrates a method for preparing enantiomerically enriched (−)-halofenate.

CPTA was prepared in five steps, as discussed above, without intermediate isolation in about 85% yield following crystallization from heptane. Resolution gave an average of 32% yield (max 50%) of >98% optically pure (−)-CPTA diastereomeric salt. After removing the resolving agent, the (−)-CPTA was esterified to give (−)-halofenate in about 55% yield using thionyl chloride and N-acetylethanolamine. By hydrolyzing the mother liquor residue with aqueous sodium hydroxide, (−)-CPTA can be recovered from the final product mother liquor and cycled back through the process. The resolving agent was isolated from water in about 90% recovery by a pH adjustment. Recovery and racemization of the (+)-CPTA using aqueous sodium hydroxide gave about 90% recovery. Overall, the first pass yield from 4-chlorophenylacetic acid was 15–17%. The entire eight-step process used three organic solvents, and three solid isolation steps.

Example 22

This example illustrates a method for preparing CPTA.

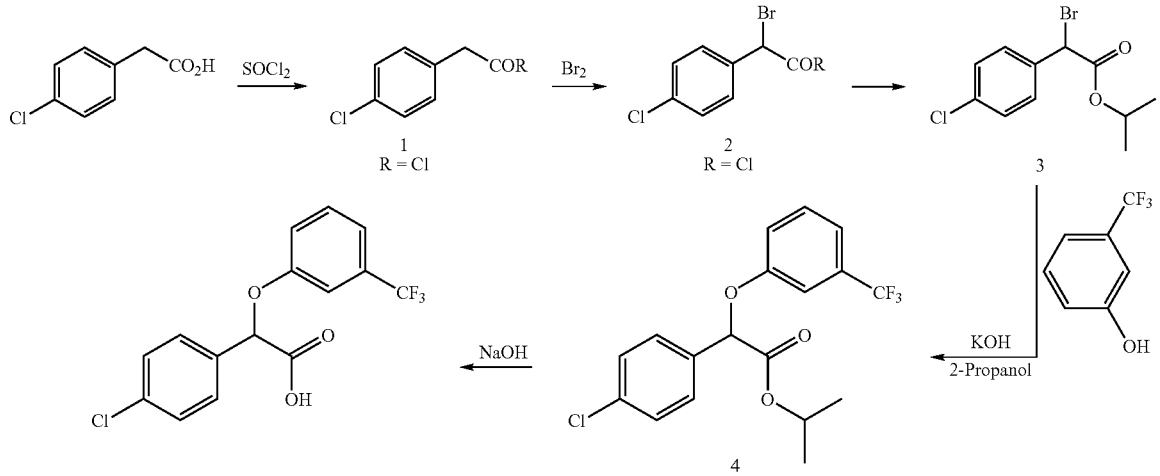

The synthetic route to CPTA is outlined above. Following bromination of the acid chloride 1 in 1,2-dichloroethane to give 2,2-propanol was added to give the isopropyl ester 3. The displacement reaction with α,α,α-trifluoro-m-cresol was accomplished using potassium hydroxide in 2-propanol. Following a water quench and wash and removal of the 1,2-dichloroethane, the liquid 3 was added to a solution of α,α,α-trifluoro-m-cresol and potassium hydroxide in 2-propanol to give 4. The 2-propanol solvent was removed, and the hydrolysis to CPTA was completed by heating with aqueous sodium hydroxide.

The sodium salt of CPTA can be isolated as a solid by simply cooling the reaction mixture. Better isolated yields were obtained, however, by isolation of the carboxylic acid. For isolation, the basic aqueous CPTA reaction mixture was acidified with hydrochloric acid, and the CPTA was extracted into 1,2-dichloroethane. Solvent exchange of the separated organic phase from 1,2-dichloroethane to heptane afforded CPTA as a white solid in approximately 85% yield from 4-chlorophenylacetic acid.

Example 23

This example shows solubility of CPTA in 1,2-dichloroethane and heptane.

Figure 11:
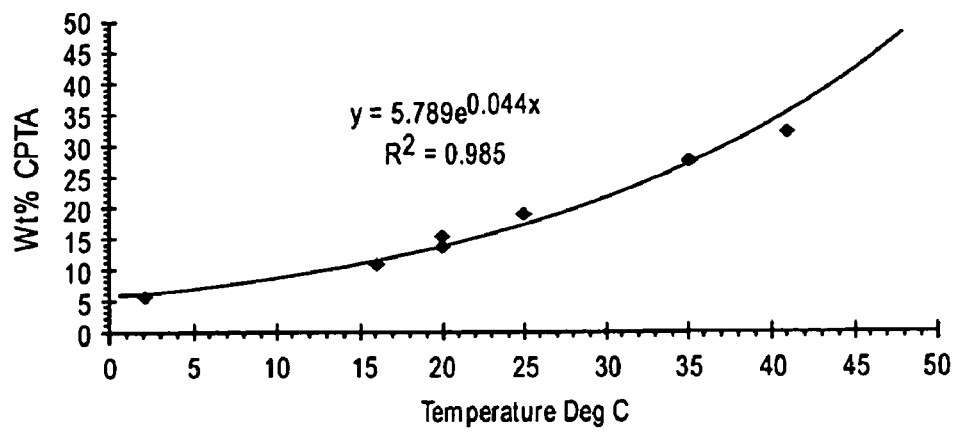
FIG. 11 is a graph showing solubility of racemic CPTA at various temperatures in 1,2-dichloroethane.
Figure 12:
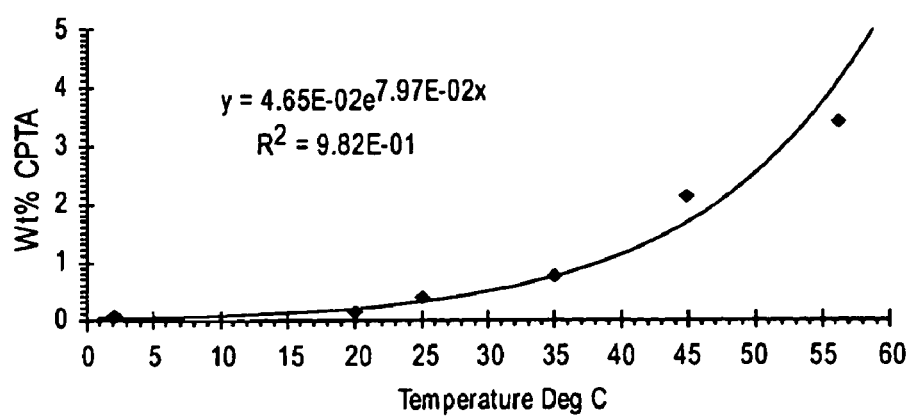
FIG. 12 is a graph showing solubility of racemic CPTA at various temperatures in heptane.

The solubility of racemic CPTA in 1,2-dichloroethane and heptane are shown in FIGS. 11 and 12, respectively. Included in the Figures are the equations for the least-squares fit of the data.

Based on the solubility profile of FIG. 11, a concentration of approximately 25 wt % CPTA in 1,2-dichloroethane at a temperature of approximately 35° C. was chosen for the CPTA extraction conditions.

CPTA crystallization from heptane was exothermic. Seeding of a solution of approximately 170 g of CPTA in 500 mL of heptane at 46° C. resulted in a temperature increase to 54° C. as the crystallization progressed. Crystallization increased the CPTA purity as determined by HPLC analysis from 93–95 to >99 area %. HPLC assay of a crystallization mother liquor, which contained 15 area % of CPTA, found less than 3% yield loss to the mother liquor. As the purity was improved by crystallization, isolated yields were high, and the loss to the mother liquor was minor.

Example 24

This example shows yield of CPTA resolution under variety of crystallization conditions.

Results of CPTA resolution using CAF D-Base under various crystallization conditions are shown in FIG. 13. Final chiral purity for each preparation, obtained after zero, one, or two recrystallizations, is in bold type. The molar ratio of the CAF D-Base was varied from 0.5 to 0.56. The amount of 2-propanol solvent listed for the crystallizations and recrystallizations are both based on the initial charge of racemic CPTA. Chiral HPLC results for both the isolated solids and mother liquors are normalized to 100%. The calculated yield and overall yield are calculated from the ratio of the (+)-enantiomer and (−)-enantiomer forms in the isolated solids and mother liquors. The actual percent yield in the last column is of weighed, dried material, and is based on a maximum yield of 50%.

Overall yields of the diastereomeric salt at >98% optical purity ranged from 28 to 35%, and averaged 32%. In one case, using the lowest ratio of resolving agent, this was obtained without recrystallization (experiment 2 in FIG. 13). The chiral purity of the first isolated solid ranged from 73% to 98%. A single recrystallization was generally sufficient to obtain the desired optical purity. A high overall yield was obtained when the mother liquor reached a 20/80 ratio of (−)-CPTA to (+)-CPTA.

FIG. 14 shows the cooling profiles for the resolution crystallizations listed in order of decreasing yield of (−)-CPTA. Experiment number in FIG. 14 corresponds to the experiment number in FIG. 13. The isolated yield of (−)-CPTA was determined using the calculated yield of FIG. 13 and the percent of (−)-CPTA in the isolated material. In general, longer hold times at low temperatures led to an increase in yield.

Use of 0.45 molar equivalents of CAF D-Base consistently gave 35–37% yield of material that was >98% optically pure without the need for recrystallization.

Example 25

This example shows a method for separating (−)-CPTA from the CAF D-Base.

To separate (−)-CPTA from the CAP D-Base, the diastereomeric salt was mixed with 1,2-dichloroethane, and aqueous hydrochloric acid was added to give a pH in the aqueous phase of less than about 2. The aqueous phase containing the hydrochloride salt of the CAF D-Base was separated. After a water wash of the organic phase, the bulk of the 1,2-dichloroethane was removed by distillation to remove residual water. Complete solvent removal gave an oil.

Example 26

This example shows a method for esterifying (−)-CPTA without any significant racemization.

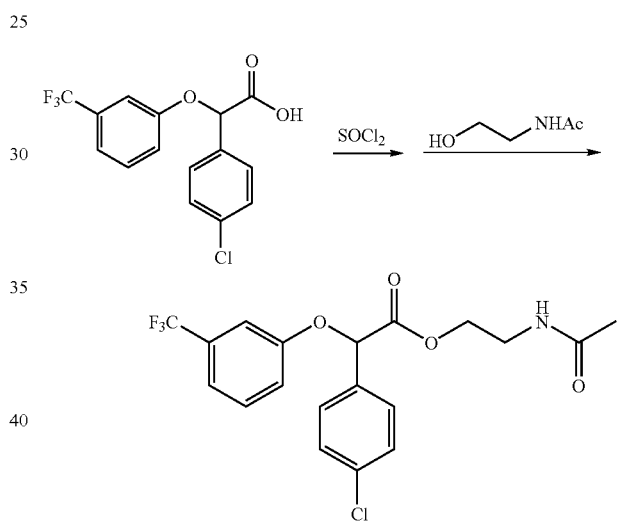

(−)-CPTA was reacted with thionyl chloride in 1,2-dichloroethane at reflux to yield a corresponding acid chloride. Reaction progress can be monitored by HPLC analysis. A small amount of distillate was removed to remove excess thionyl chloride. The mixture was cooled, and a large excess of vacuum distilled N-acetylethanolamine was added. Stirring at ambient temperature gave (−)-halofenate.

The esterification reaction mixture was quenched by adding the reaction mixture to an aqueous potassium carbonate solution. (−)-Halofenate was isolated by solvent exchange and crystallization from the 6:1 heptane:2-propanol. Results are summarized in FIG. 15.

First crop isolated yields ranged from 47 to 59% and averaged 55%. This isolated yield represents a reaction yield of 75 to 80% for this step. A second crop afforded a higher overall yield; however, the product quality was poorer with the second crop material.

Molar accountability of the CPTA loaded, found as isolated halofenate, and halofenate and CPTA in the mother liquor, ranged from 90 to 99%.

Example 27

This example shows a method for recovering and recycling (+)-CPTA.

Heating CPTA in aqueous base caused racemization. The remaining CPTA from the resolution step in Example 25 was approximately 47% ee of the (+)-enantiomer, which also contains residual CAF D-Base.

To recover and racemize the (+)-CPTA, the 2-propanol solvent was removed and replaced with 1,2-dichloroethane. Washing with water at a pH below about 2 removed the CAF-D-Base for subsequent recovery. Aqueous sodium hydroxide was added, and the aqueous solution heated to reflux. The 1,2-dichloroethane was either removed by distillation prior to the addition of the basic solution, or by a phase separation following addition of the basic solution. An 89% yield of racemic CPTA was isolated from heptane after heating an aqueous solution for four hours with 1.4 molar equivalents of sodium hydroxide. Isolation of CPTA as a crystallized intermediate provided a more consistent quality feed for the resolution step.

Figure 16:
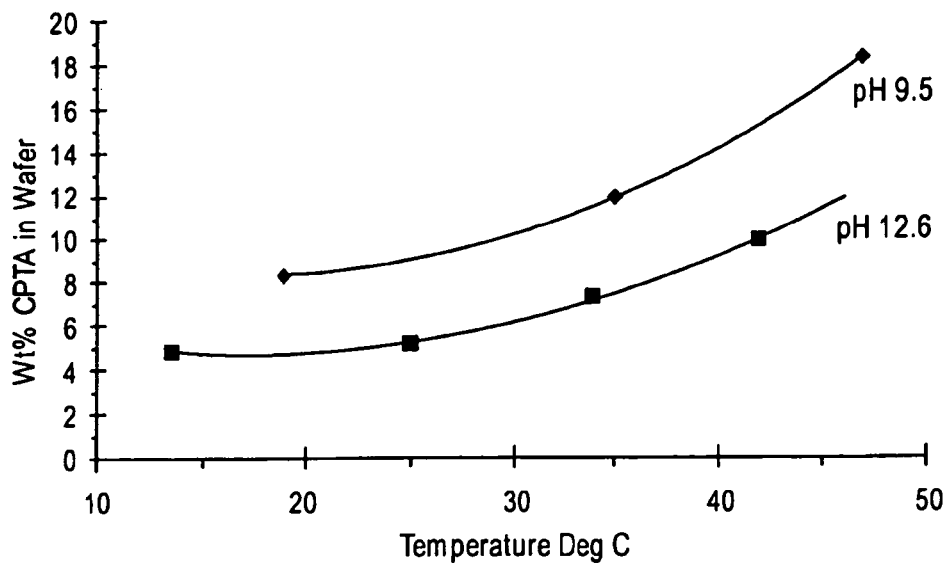
FIG. 16 is a graph showing solubility of racemic CPTA sodium salt at various temperatures in water.

The solubility of the sodium salt of racemic CPTA in water, determined and expressed as the acid form, is shown in FIG. 16. Addition of the isolated sodium salt to water gave a pH of about 9.5, and the solubility profile shown in the upper solubility curve. Addition of a small amount of sodium hydroxide to give a pH of about 12.6 decreased the aqueous solubility to that shown on the lower curve.

Example 28

This example shows a method for producing CPTA from (+)-halofenate.

Addition of from 1 to 3 molar equivalents of sodium hydroxide to about 10 wt % of 87% ee (+)-halofenate in water and warming to 50 to 60° C. resulted in a substantially complete hydrolysis to CPTA. Partial racemization to give approximately 70% ee (+)-CPTA occurred (Time=0 of FIG. 17). The solution was heated to reflux, and the enantiomeric ratio monitored over time. With 3 molar equivalents of base, almost complete racemization (<3% ee by the chiral HPLC analysis method) occurred in less than 2 hours at reflux. The pH dropped from 12.8 to 12.6 over the course of the racemization. A slightly longer reaction time was required with 2 molar equivalents (pH 12.6 to 11.6). With 1 molar equivalent, racemization stopped at approximately 60 to 70% ee, with a final pH of 9.4.

Use of 0.5 molar equivalents of sodium hydroxide left approximately 40% of the halofenate unhydrolyzed after 2 hours at 60° C.; heating to reflux overnight left approximately 1% halofenate at a final pH of 4.8. This did not significantly minimize racemization. The amount of CPTA produced was 72.6% ee of the (+)-enantiomer.

Example 29

This example illustrates a method for recovering (−)-CPTA from (−)-halofenate crystallization mother liquor.

As noted previously and shown in FIG. 15, the (−)-halofenate crystallization mother liquor contains a large amount of (−)-halofenate and (−)-CPTA. By hydrolysis of the (−)-halofenate, additional (−)-CPTA can be generated as feed for the resolution step.

Hydrolysis of a (−)-halofenate crystallization mother liquor (88.3% ee of (−)-halofenate) at 50° C. and a final pH of 12.7 rapidly gave 65.8% ee (−)-CPTA. The (−)-CPTA was recovered as the CAF D-Base diastereomeric salt (96.4% ee) by addition of CAF D-Base to a 2-propanol solution. From the amount of diastereomeric salt initially loaded, 55 mol % was obtained as (−)-halofenate, 28% was recovered as the (−)-CPTA/CAF D-Base salt, and 14 mol % remained as CPTA in the mother liquor.

Example 30

This example illustrates a method for recovering CAF D-Base.

The CAF D-Base is found in the acidic phase from separation of (−)-CPTA from the diastereomeric salt, and from the acidic wash step of the CPTA recovery from the resolution mother liquors. Basification with aqueous sodium hydroxide to a pH greater than about 12 resulted in precipitation with good recovery in a form that was easily filtered. Results are shown in FIG. 18. Recovery from the diastereomeric salt was generally greater than 90%; recovery from the resolution mother liquor was lower. Concentrations in the aqueous solution ranged from about 5 to 20%.

The enantiomeric purity of the CAF D-Base can be determined by careful analysis of the melting point by DSC (D. Pitre, M. Nebuloni, and V. Ferri; *Arch. Pharm. (Weinheim)* 324, 525 (1991)). As the conglomerate of the (+)- and (−)-forms, e.g., racemate, melts more than 20° C. lower than the pure enantiomer, melting point was found to be a sensitive method for assessing enantiomeric purity. However, measurement of the enantiomeric purity of two of the samples by chromatographic separation of a derivative showed no loss of chiral purity. The enantiomeric purity of the recovered CAF D-Base, near the detection limit of the HPLC analysis method, was indistinguishable from the source material.

Example 31

This example illustrates another method for preparing racemic CPTA.

A 500-mL round-bottom flask in a heating mantel and fitted with an overhead stirrer and condenser was charged with 73.28 g (0.430 mol) of 4-chlorophenylacetic acid, 70 ml, of 1,2-dichloroethane, and 41 mL (0.56 mol) of thionyl chloride. The mixture was warmed at 50 to 55° C. for 19 h. The reaction mixture was analyzed by HPLC analysis. To the solution of acid chloride was added 29 mL (0.57 mol) of bromine, and the solution was warmed at 70 to 75° C. for 20 h. The resulting α-bromo product was cooled in an ice bath and 100 mL (1.31 mol) of 2-propanol was added dropwise. The maximum temperature reached was 17° C. After cooling to 4° C., the reaction mixture was added to water. The solution was warmed to ambient temperature, and the aqueous layer was removed. The organic phase was washed with 37 mL of water. The separated 1,2-dichloroethane solution was evaporated to give 134.1 g of an oil.

A 1-L round-bottom flask with an overhead stirrer was charged with 34.0 g (0.515 mol) of 85% potassium hydroxide and 370 mL of 2-propanol. The mixture was warmed to 41° C. using a water bath to dissolve much of the solid. The mixture was cooled in an ice bath, and 73.8 g (0.455 mol) of α,α,α-trifluoro-m-cresol was added dropwise. The maximum temperature reached was 13° C. The solution was cooled to 5° C. before the dropwise addition of 134.1 g of the oil obtained above. The material was rinsed in with 18 g of 2-propanol. The slurry was evaporated to a residue, then charged with 250 mL of water and 42.8 g (0.535 mol) of 50% aqueous sodium hydroxide. The mixture was heated to reflux for 1 h.

After cooling to ambient temperature, the mixture was diluted with 250 mL of 1,2-dichloroethane, and the pH was decreased to 0.3 by the dropwise addition of 71 g (0.72 mol) of 37% hydrochloric acid. After a phase separation, the solvent was removed from the 1,2-dichloroethane phase to give 202.2 g of residue. The residue was treated with 131 g of heptane, and evaporated to a residue of 164 g. The process was repeated with 97 g of heptane, giving 160 g of an oil. The residual oil was stirred at ambient temperature with 257 g of heptane to give a slurry, which was chilled in an ice bath before isolation of the solid by filtration. The filter cake was washed with 49 g of heptane, then dried under a vacuum to give 125.58 g (0.380 mol, 88% yield) of CPTA.

Example 32

This example illustrates a method for preparing a racemic mixture of compound 4 of Example 22.

A 50-mL round-bottom flask equipped with a magnetic stirrer and reflux condenser was charged with 2.10 g (6.35 mmol) of racemic CPTA, 21 g of 2-propanol, and 0.50 g (4.2 mmol) of thionyl chloride. HPLC analysis after 90 minutes at reflux indicated 84.2 area % of 7 and 12.7 area % of CPTA. An additional 1.0 g (8.4 mmol) of thionyl chloride was added to give less than 1 area % of CPTA. The solution was cooled to ambient temperature and treated with 1.0 g (12 mmol) of solid sodium bicarbonate. The solvent was evaporated, and the residue dissolved in 25 mL of toluene. After washing with water (2×10 mL), the solvent was evaporated to a residue of 2.31 g (6.2 mmol, 98% yield) of compound 4 of Example 22 (95.8 area % of 7, 2.4 area % of toluene).

Example 33

This example illustrates a method for determining solubility of racemic CPTA.

A 100 mL water jacketed resin pot with a magnetic stirrer was connected to a recirculating water bath and charged with 9.44 g of racemic CPTA and 16.78 g of 1,2-dichloroethane. The bath temperature was warmed to 35° C., and the slurry was stirred for one hour. The agitator was shut off, and the solid was allowed to settle for 30 min. A 0.1360 g sample of the supernate was removed and diluted to 25.00 mL with acetonitrile, and the solution was assayed by HPLC analysis. Results for this and a series of other measurements are shown in FIGS. 11 and 19. For analysis at about 2° C., a 0.54 g-sample of CPTA in 1.92 g of 1,2-dichloroethane was stored in a refrigerator overnight before analysis of the supernate by HPLC analysis. The solubility of CPTA in heptane, included in FIG. 19 shown in FIG. 12, was determined in a similar fashion.

Example 34

This example illustrates a method for resolving a racemic mixture of CPTA.

A 1-L bottom-drain reactor was charged with 48.2 g (146 mmol) of CPTA, 16.4 g (77.3 mmol) of (1R,2R)-(−)-2-amino-1-(4-nitrophenyl)-1,3-propanediol (CAF D-Base), and 193 g of 2-propanol. The slurry was heated to 70° C. to give a solution, then cooled to 60° C. and held for 1 h. The resulting slurry was cooled at 0.25° C./min to a jacket temperature of 2° C. and held for 14 h; the internal temperature was 4° C. The solid was isolated by vacuum filtration and rinsed with 27 g of 2-propanol. The mother liquor and wash solution was sampled for HPLC analysis, and the results are shown in FIG. 13. The 50.48-g wetcake was reloaded to the 1-L reactor with 193 g of 2-propanol, and the slurry warmed to a gentle reflux with a jacket temperature of 85° C. to give a solution. The solution was sampled for HPLC analysis; the results are listed in FIG. 13. A slurry formed upon cooling to 65° C. After warming to 68° C. for 30 min, the slurry was cooled to 40° C. at 0.25° C./min, then to 18° C. at 0.4° C./min, then to 2° C. at 1° C./min. (In other preparations, linear cooling rates recorded in FIG. 14 were used.) The solid was isolated by vacuum filtration, rinsed with 18 g of 2-propanol, and dried under vacuum to give 27.29 g (50.4 mmol, 34.5% yield) of (−)-CPTA/CAF D-Base. HPLC analysis results for the isolated solid and mother liquor and wash are included in FIG. 13.

Example 35

This example illustrates preparation and resolution of racemic CPTA from halofenate.

A 1-L round-bottom flask with an overhead stirrer was charged with 129.75 g (0.312 mol) of racemic halofenate, 325 g of water, and 32.6 g (0.408 mol) of 50% aqueous sodium hydroxide. The slurry was heated to 60° C. for 1 hour to give a solution, then cooled. At a temperature of 40° C., 328.5 g of 1,2-dichloroethane and 44 g (0.45 mol) of 37% hydrochloric acid were added, and the two-phase mixture was cooled to 29° C. The pH of the aqueous phase was 0.85. The organic phase was separated and washed with 250 mL of water, then evaporated to a residue of 118.2 g. 2-Propanol (149 g) was added, and evaporated to a residue of 131.2 g. The residue, containing theoretically 103.2 g of racemic CPTA based on the amount of halofenate loaded, was charged to a 1-L bottom-drain reactor with 33.10 g (0.1556 mol) of CAF D-Base and 400 g of 2-propanol. The mixture was warmed to 67° C. to give a light slurry, then cooled to 1° C. at 0.075° C./min. The mixture was chilled to −7° C., and the solid isolated by vacuum filtration and washed with 60 mL of 2-propanol. HPLC analysis results of the isolated solid and the 492.8-g mother liquor and wash solution are shown in FIG. 13 (experiment 9). The 92.74-g wetcake was reloaded to the 1-L reactor along with 477 g of 2-propanol, and the mixture heated to 75° C. to give a solution. The solution was cooled to 5° C. at 0.5° C./min, and the crystallized solid isolated by vacuum filtration, rinsed with 60 mL of 2-propanol, and dried to give 51.81 g (0.0956 mol, 31% yield) of the (−)-CPTA CAF D-Base diastereomeric salt. HPLC analysis results for the isolated solid and 529.9 g of mother liquor and wash solution are included in FIG. 13.

Example 36

This example illustrates a method for racemizing (+)-CPTA and recovering racemic CPTA.

The resolution and recrystallization mother liquors from the resolution of 103.2 g of CPTA described in Example 35 above, containing 71.6 g (0.217 mol) of CPTA (44% ee of the (+)-enantiomer) based on the yield and purity of the isolated diastereomeric salt, was evaporated to a residue of 108.7 g. The residue was treated with 176 g of 1,2-dichloroethane, 35.2 g of water, and 6.8 g of 37% hydrochloric acid. The organic phase was removed and evaporated to a residue to 79.0 g. Water (80 g) was added, and the solvent evaporated to a residue of 78.1 g. The residue was treated with 141.9 g of water and 24.6 g (0.308 mol) of 50% aqueous sodium hydroxide, and the solution was heated to reflux for 4 hours to give a racemate by chiral HPLC analysis. The solution was cooled and treated with 140 ml, of 1,2-dichloroethane and 32.0 g (0.325 mol) of 37% hydrochloric acid. The organic phase was removed and evaporated to a residue of 80.1 g, which was treated with 250 mL of heptane in a 40° C. water bath to give a slurry. The solid was isolated by vacuum filtration and dried to give 63.83 g (0.193 mol, 89% yield) of racemic CPTA. Resolution of a sample gave results consistent with those of fresh CPTA (entry 10 of FIG. 13).

Example 37

This example illustrates a method for isolating (−)-CPTA from the diastereomeric salt.

A 500-mL flask with a magnetic stirrer was charged with 40.0 g (73.7 mmol) of (−)-CPTA/CAF D-Base, 100 g of 1,2-dichloroethane, 40 g of water and 7.6 g (77 mmol) of 37% hydrochloric acid. After complete dissolution of the solid, the lower organic phase was removed and washed with 10 mL of water. The pH of the combined aqueous phase was 0.9. HPLC assay of 128.2 g of the organic phase found 24.32 g (73.6 mmol, 99.8% of theory) of (−)-CPTA as a solution in 1,2-dichloroethane.

Example 38

This example illustrates a vacuum purification of N-acetylethanolamine.

A 50-mL round-bottom flask equipped with a magnetic stirrer, heating mantel and a short path distillation head was charged with 29.09 g of N-acetylethanolamine and placed under a vacuum of approximately 0.8 torr. Bubbles formed as the liquid was heated, although no condensate was collected. Distillate was collected at a head temperature of approximately 130° C. to afford 26.71 g (92% recovery) of N-acetylethanolamine as a clear liquid.

Example 39

This example illustrates a method for producing (−)-halofenate.

A 500-mL round-bottom flask with a magnetic stirrer was charged with 35.5 g (65.4 mmol) of the (−)-CPTA/CAF D-Base diastereomeric salt (99.4% ee), 89.0 g of 1,2-dichloroethane, and 35.5 mL of water. To the slurry was added 6.7 g (68 mmol) of 37% hydrochloric acid, and the mixture was stirred at ambient temperature to give two clear phases. The lower organic phase was removed and washed with 7.0 g of water. The organic phase was evaporated to a residue of 26.13 g, then dissolved in 55.6 g of 1,2-dichloroethane and placed in a 250-mL round-bottom flask in a heating mantel with a magnetic stirrer and fitted with a reflux/distillation head. HPLC assay of the solution found 22.06 g (66.7 mmol, 102% of theory) of CPTA. To the solution was added 7.5 mL (100 mmol) of thionyl chloride, and the solution was heated to reflux for 2 hours. Heating was continued to collect 6.1 g of distillate. The solution was cooled to ambient temperature, then chilled in an ice bath for the addition of 25.85 g (251 mmol) of distilled N-acetylethanolamine (KF analysis 1176 and 1288 ppm water). The temperature rose to about 26° C. after the addition. The solution was added slowly with stirring to 9.90 g (71.6 mmol) of potassium carbonate in 36 g of water chilled in an ice bath. The maximum temperature reached was 15° C. The reaction mixture was rinsed in with 5 mL of 1,2-dichloroethane. The lower organic phase was removed and washed with 37 mL of water. The solution was evaporated to give an oil (32.84 g). The oil was treated with 54 g of heptane, and the solvent was removed to give 31.56 g of a solid residue. To the solid was added 76 g of heptane, and the solvent was removed to give 29.19 of a solid residue. The solid was dissolved in 28 mL of 2-propanol at 40° C., then diluted with an additional 28 mL of 20 propanol and 334 mL of heptane. Cooling to ambient temperature gave a thin slurry. A thick slurry formed upon cooling in an ice bath. After stirring for 2 hours, the solid was isolated by vacuum filtration, rinsed with 29 g of heptane, and dried to give 14.21 g (34.2 mmol, 52.3% yield) of (−)-halofenate. No (+)-halofenate was detected by chiral HPLC analysis (>99.8% ee).

HPLC assay of 294.1 g of the mother liquor and wash found 11.2 g of halofenate and 1.26 g of CPTA. The solvent was evaporated, and 12.47 g of the residue was dissolved in 14 mL of 2-propanol. Addition of 84 mL of heptane gave a slurry after stirring overnight at ambient temperature. The slurry was chilled in an ice bath and the solid was collected, rinsed with 9 g of heptane, and dried to give 5.64 g (13.6 mmol, 20.7% yield, 89.9% halofenate and 3.9% CPTA by HPLC analysis, 99.6% ee) of (−)-halofenate. HPLC assay of 81.74 g of the mother liquor and wash found 3.66 g (8.8 mmol, 13.5%) of halofenate and 0.93 g (2.8 mmol, 4.8%) of CPTA.

Example 40

This example illustrates a method for isolating racemic CPTA sodium salt.

The mother liquors from a resolution crystallization and recrystallization containing in theory 63.9 g (0.193 mol) of CPTA based on the resolution recovery was evaporated to a residue of 91 g. The residue was dissolved in 146 g of 1,2-dichloroethane and treated with 28.6 g of water and 6.3 g of 37% hydrochloric acid at 40° C. The 219 g organic phase was evaporated to a residue of 71.86 g. To the residue was added 120 g of water and 21.5 g (0.269 mol) of 50% sodium hydroxide. The solution was heated to reflux, then allowed to cool to ambient temperature to give a thick slurry. The solid that formed upon cooling was isolated by vacuum filtration, rinsed with 25 mL of water, then dried to give 31.78 g (0.0901 mol, 46.7% recovery) of the sodium salt of CPTA. Chiral HPLC analysis found that the material was racemic. HPLC assay of the 188.6 g mother liquor and wash found 28.3 g (0.0856 mol, 44.4%) of CPTA.

Example 41

This example illustrates a method for determining the solubility of racemic CPTA sodium salt.

A 100-mL water jacketed resin pot with a magnetic stirrer was connected to a recirculating water bath and charged with 3.48 g of the racemic CPTA sodium salt and 20.0 g of water. The bath temperature was warmed to 35° C., and the slurry was stirred for one hour. The agitator was shut off, and the solid was allowed to settle for 30 min. The pH was 9.4. A 0.3036 g-sample of the supernate was removed and diluted to 25.00 mL with acetonitrile, and the solution was assayed by HPLC analysis. Analysis was repeated at 47° C. and at 19° C. An additional 3.01 g of CPTA sodium salt was added to maintain a slurry at the higher temperature, and 25 g of water was added to give a thinner slurry at the lower temperature. The pH was increased to 12.7 at ambient temperature by the addition of 50% aqueous sodium hydroxide, and the analysis was continued at 13.5, 25, 34, and 42° C. Results are shown in FIGS. 16 and 20.

Example 42

This example illustrates hydrolysis and racemization of (+)-halofenate.

Figure 17:
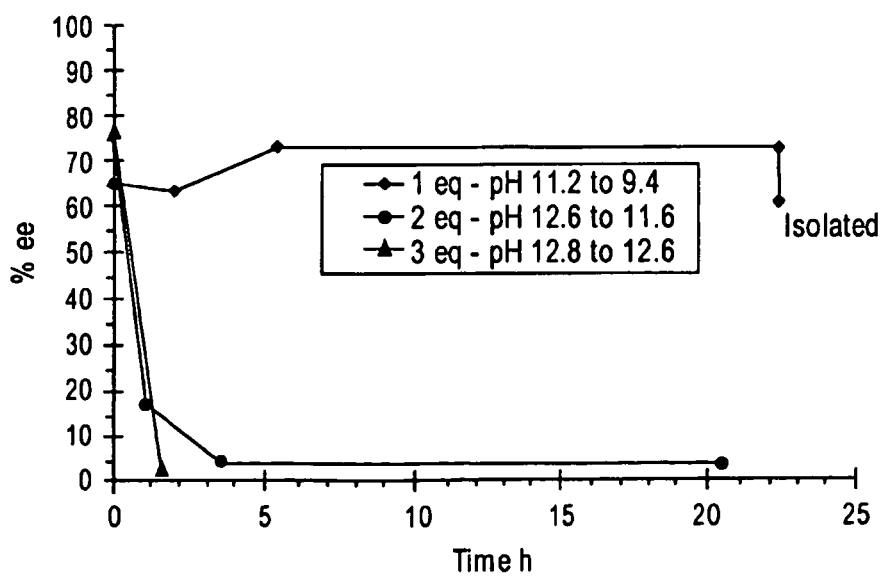
FIG. 17 is a graph showing CPTA racemization profile at various pH during hydrolysis of (−)-halofenate.

A 250-mL round-bottom flask equipped with a magnetic stirrer and heating mantel was charged with 7.28 g (17.5 mmol) of (+)-halofenate (86.9% ee), 72.2 g of water, and 4.21 g (52.6 mmol) of 50% aqueous sodium hydroxide. The slurry was heated to 50 to 60° C. The pH of the resulting solution was 12.8. Chiral HPLC analysis showed 80.4% of (+)-CPTA and 10.5% of (−)-CPTA. The solution was heated to reflux for 90 minutes. Chiral HPLC analysis showed 49.6% of (+)-CPTA and 47.0% of (−)-CPTA. The pH was 12.6. After cooling to ambient temperature, approximately 50 mL of 1,2-dichloroethane was added, and the pH was adjusted to 0.8 by the addition of 7.3 g (74 mmol) of 37% hydrochloric acid. The organic phase was evaporated to a residue of 6.0 g. The residue was treated with 25 mL of heptane, warmed to dissolve the oil, and then cooled in an ice bath. The solid was collected by vacuum filtration and dried to give 5.10 g (15.4 mmol, 88% yield) of racemic CPTA. Data for this and two similar hydrolyses are shown in FIGS. 17 and 21.

Similarly, heating 6.75 g (16.3 mmol) of (+)-halofenate with 0.65 g (8.1 mmol) of 50% aqueous sodium hydroxide in 67.5 g of water for 2 hours at 60° C. gave 37.5% of halofenate and 54.2% of CPTA. Heating to reflux overnight gave 92.1% of CPTA and 1.1% of halofenate, with a final pH of 4.8. Chiral HPLC analysis found an 80.3/12.8 ratio of (+)/(−)-CPTA.

Example 43

This example illustrates preparation of (−)-halofenate with recovery of the (−)-CPTA/CAF D-Base diastereomeric salt from the (−)-halofenate crystallization mother liquors.

A 1-L round bottom flask with magnetic stirring was charged with 50.0 g (92.3 mmol) of the (−)-CPTA/CAF D-Base diastereomeric salt (97.1% ee), 124 g of 1,2-dichloroethane, 50 mL of water, and 9.6 g (98 mmol) of 37% hydrochloric acid. The organic phase was separated and washed with 50 mL of water, then placed in a 250-mL round-bottom flask in a heating mantel with a magnetic stirrer. A reflux/distillation head was attached, and the solution was heated to remove 35.4 g of distillate by distillation. After cooling to 40° C., the solution was diluted with 25 mL of 1,2-dichloroethane, and 11 mL (150 mmol) of thionyl chloride was added. After heating at reflux for 2 hours and removing 22.6 g of distillate, the solution was cooled in an ice bath for the dropwise addition of 38.6 g (374 mmol) of distilled N-acetylethanolamine. The reaction temperature rose from 7 to 18° C. during the addition. After stirring overnight at ambient temperature, the solution was added with stirring to 12.7 g of potassium carbonate in 51 mL of water chilled in an ice bath. The organic phase was removed and washed with 51 g of water. The organic phase (85.2% of halofenate and 6.1% CPTA by HPLC analysis) was evaporated to an oil of 44.3 g, treated with 133 g of heptane, then evaporated to a solid of 43.3 g. The solid residue was dissolved in 61.5 g of 2-propanol and charged to the 1-L bottom-drain reactor along with 320 g of heptane, warmed to 50° C., and cooled at 3° C./min to 20° C., then at 1° C./min to −3° C. solution became hazy at 27° C., and a thick slurry formed at 15° C. The solid was isolated by vacuum filtration, washed with 40 mL of heptane containing 5 mL of 2-propanol, and dried to give 21.01 g (50.6 mmol. 55% yield, 98.93% by HPLC) of (−)-halofenate (99.9% ee). The 395.7 g mother liquor and wash solution, containing 14.65 g (35.3 mmol) of halofenate (88.3 % ee) and 1.78 g (5.4 mmol) of CPTA by HPLC assay, was evaporated to a residue of 21.57 g. The residue was heated to 50° C. with 100 mL of water and 5.0 g (63 mmol) of 50% aqueous sodium hydroxide to give a solution. HPLC analysis after about 10 minutes found 83.6% of CPTA and 0.3% of halofenate. The solution was cooled, diluted with 50 mL of 1,2-dichloroethane, and the pH decreased from 12.7 to 1.6 with 7.3 g (74 mmol) of 37% hydrochloric acid. After washing with 30 mL of water, the 72.9 g organic phase, containing 11.32 g (34.2 mmol) of CPTA by HPLC assay, was evaporated to a residue, treated with 36 g of heptane, then evaporated to a residue of 14.9 g. The oily residue was dissolved in 38 g of heptane with heating. Cooling gave an oil. The solvent was removed and the residual oil dissolved in 34.8 g of methylcyclohexane. An oil formed with cooling. The solvent was removed and replaced with 45.6 g of 2-propanol. Chiral HPLC analysis found 65.8% ee of (−)-CPTA (a (+)/(−)-ratio of 16.9/81.6). To the solution at ambient temperature was added 6.50 g (30.6 mmol) of CAF D-Base. A thick slurry rapidly formed. The slurry was warmed to 40° C. with stirring, then cooled in an ice bath and the solid isolated by a vacuum filtration, washed with 7 g of 2-propanol, and dried to give 13.91 g (25.7 mmol) of (−)-CPTA/CAF D-Base diastereomeric salt, which corresponds to 28% recovery of the 50.0 g of salt initially loaded. The (+)/(−)-CPTA ratio was 1.77/97.86. HPLC assay of the 45.34-g mother liquor and wash solution found 4.34 g (13.1 mmol) of CPTA, which corresponds to 14 mol % of the 50.0 g of salt initially loaded.

Example 44

This example illustrates a process for recovering CAF D-Base from CPTA/CAF D-Base salt.

A 1-L round-bottom flask with a magnetic stirrer was charged with 80.16 g (0.148 mol) of the (−)-CPTA/CAF D-Base salt, 237 g of 1,2-dichloroethane, and 80 mL of water. To the slurry was added 15.2 g (0.154 mol) of 37% hydrochloric acid, giving two clear phases. The pH of the aqueous layer was 1.2. The lower organic layer was removed and washed with 16 mL of water. The combined aqueous phase (140.7 g) was treated with 12.9 g (0.161 mol) of 50% aqueous sodium hydroxide to reach a pH of 12.1. The resulting slurry was filtered and the solid was rinsed with 25 mL of water and dried to give 30.79 g (0.145 mol, 98% recovery) of CAF D-Base (mp 160.4-161.0° C.).

Example 45

This example illustrates a process for recovering CAF D-Base from the resolution mother liquor.

A 60.0 g sample of racemic CPTA was resolved with 20.88 g of CAF D-Base in 240 g of 2-propanol as described above to give a 74.7 g wetcake. The wetcake was recrystallized in 218 g of 2-propanol to give 32.35 g (32.8% yield) of (−)-CPTA/CAF D-Base salt. The mother liquor and wash solutions from the crystallization and recrystallization, theoretically containing 40.32 g of CPTA and 8.23 g (38.8 mmol) of CAF D-Base from the amount of salt obtained, was evaporated to a residue of 72.9 g. The residue was dissolved in 265 g of 1,2-dichloroethane, 50 mL of water, and 4.0 g (40.6 mmol) of 37% hydrochloric acid. The aqueous layer was separated, and the pH was increased from 0.6 to 12.3 by the addition of 3.88 g (48.5 mmol) of 50% aqueous sodium hydroxide. The resulting slurry was filtered and the solid was collected and rinsed with water to give 7.12 g (33.6 mmol, 87% recovery) of CAF D-Base (mp 162.4–163.0° C.).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A process for enantioselectively producing a α-(phenoxy)phenylacetate compound of the formula:

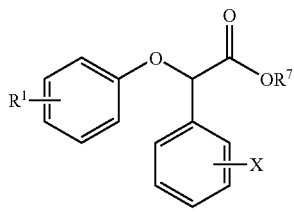

said method comprising:
(a) resolving an enantiomeric mixture of a α-(phenoxy) phenylacetic acid of the formula:

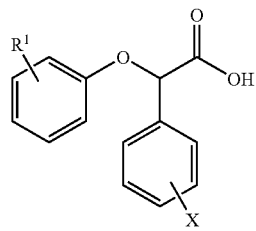

using an enantiomerically enriched chiral amine compound;
to produce an enantiomerically enriched α-(phenoxy) phenylacetic acid, wherein the total amount of enantiomerically enriched chiral amine compound used is less than 0.5 molar equivalents with respect to the α-(phenoxy)phenylacetic acid compound;
(b) producing an enantiomerically enriched activated α-(phenoxy)phenylacetic acid derivative by contacting the enantiomerically enriched α-(phenoxy)phenylacetic acid with a carboxylic acid activating reagent; and
(c) contacting the enantiomerically enriched activated α-(phenoxy)phenyl-acetic acid derivative with a compound of the formula $(R^7-O)_wM$ to produce the α-(phenoxy)phenyl-acetate compound,
wherein
$R^1$ is alkyl or haloalkyl;
X is halide;
$R^7$ is heteroalkyl;
M is hydrogen or a metal; and
the subscript w is the oxidation state of M.

2. The method of claim 1, wherein the α-(phenoxy) phenylacetate compound is (−)-halofenate.

3. The method of claim 1, wherein said step (a) resolving the enantiomeric mixture of the α-(phenoxy)phenylacetic acid comprises:

(a) producing a crystallization solution mixture comprising a solid enantiomerically enriched acid-base salt of a first enantiomer by contacting the enantiomeric mixture of the α-(phenoxy)phenylacetic acid compound with the enantiomerically enriched chiral amine compound under conditions sufficient to produce the ratio of the amount of first enantiomer to the amount of the second enantiomer in the salt is at least about 3:1, wherein the total amount of enantiomerically enriched chiral amine compound used is less than 0.5 molar euuivalents with respect to the α-(phenoxy)phenylacetic acid compound, and
(b) separating the solid acid-base salt of the first enantiomer from the solution mixture at a temperature where the concentration of an acid-base salt of the second enantiomer of the α-(phenoxy)phenylacetic acid compound is near or below its saturation point.

4. The method of claim 3, wherein said step (a) of producing the crystallization solution mixture comprising the solid enantiomerically enriched acid-base salt of the first enantiomer comprises:
(i) heating the solution mixture to a temperature above the nucleation temperature of a first enantiomer; and
(ii) subsequently lowering the solution mixture temperature to a temperature at or below the nucleation temperature of the first enantiomer to an enantiomerically enriched α-(phenoxy)phenylacetic acid.

5. The method of claim 3, wherein said step (b) of separating the solid acid-base salt of the first enantiomer is conducted at a temperature near or above a saturation temperature of an acid-base salt of the second enantiomer.

6. The method of claim 1 further comprising recovering the chiral amine compound by removing the chiral amine compound from the separated solid acid-base salt of the first enantiomer.

7. The method of claim 6, wherein the enantiomerically enriched chiral amine compound used in producing the acid-base salt of said step (a) comprises the recovered chiral amine compound.

8. The method of claim 1 further comprising racemizing at least a portion of the second enantiomer in the separated solution mixture by contacting the second enantiomer with a base.

9. The method of claim 8, wherein the enantiomeric mixture of the α-(phenoxy)phenylacetic acid compound used in said step (a) comprises a racemized α-(phenoxy) phenylacetic acid compound.

10. The method of claim 1, wherein the chiral amine compound is of the formula:

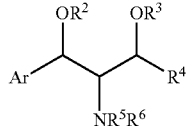

wherein
each of $R^2$ and $R^3$ is independently hydrogen or alkyl; or $R^2$ and $R^3$ together with atoms to which they are attached to form a heterocyclic ring moiety;
$R^4$ is hydrogen or alkyl;
each of $R^5$ and $R^6$ is independently hydrogen or alkyl, or one of $R^5$ or $R^6$ is an amine protecting group; and
Ar is aryl.

11. The method of claim 1, wherein the α-(phenoxy) phenylacetic acid is an enantiomeric mixture of 4-chloro-α-(3-trifluoromethylphenoxy)phenylacetic acid, said method comprising:
(a) producing a crystallization solution mixture comprising an enantiomerically enriched acid-base salt of (−)-4-chloro-α-(3-trifluoromethylphenoxy)phenylacetic acid by contacting the enantiomeric mixture of 4-chloro-α-(3-trifluoromethylphenoxy)phenylacetic acid with less than 0.5 molar equivalent of an enantiomerically enriched (1R,2R)-2-amino-1-(4-nitrophenyl)-1,3-propanediol in about 4 grams of an alcoholic solvent per gram of (−)-4-chloro-α-(3-trifluoromethylphenoxy)phenylacetic acid;
(b) separating the enantiomerically enriched acid-base salt from the solution mixture which is enriched with (+)-4-chloro-α-(3-trifluoromethylphenoxy)phenylacetic acid; and
(c) removing (1R,2R)-2-amino-1-(4-nitrophenyl)-1,3-propanediol from the acid-base salt to produce enantiomerically enriched (−)-4-chloro-α-(3-trifluoromethyl-phenoxy)phenylacetic acid.

12. The method of claim 11, wherein the alcoholic solvent is isopropanol.

13. The method of claim 12, wherein about 0.47 molar equivalent or less of (1R,2R)-2-amino-1-(4-nitrophenyl)-1,3-propanediol is used to form the acid-base salt.

14. The method of claim 13, wherein said step (a) of producing a solution mixture comprising an enantiomerically enriched acid-base salt of (−)-4-chioro-α-(3-trifluoromethyl-phenoxy)phenylacetic acid comprises heating the solution mixture to a temperature at or above a nucleation temperature of the (−)-acid-base salt.

15. The method of claim 14, wherein said step (b) of separating the enantiomerically enriched acid-base salt is performed at a temperature near or above a saturation temperature of an acid-base salt of the (+)-enantiomer.

16. The method of claim 12, wherein the enantiomerically enriched (1R,2R)-2-amino-1-(4-nitrophenyl)-1,3-propanediol comprises at least a portion of (1R,2R)-2-amino-1-(4-nitrophenyl)-1,3-propanediol that is removed from the acid-base salt of said step (c).

17. The method of claim 12 further comprising racemizing at least a portion of (+)-4-chloro-α-(3-trifluoromethylphenoxy)phenylacetic acid obtained in said step (b).

18. The method of claim 17, wherein the enantiomeric mixture of 4-chloro-α-(3-trifluoromethylphenoxy)phenylacetic acid comprises at least a portion of (+)-4-chloro-α-(3-trifluoromethylphenoxy)phenylacetic acid that is racemized.

* * * * *